(12) United States Patent
Romo et al.

(10) Patent No.: US 10,080,576 B2
(45) Date of Patent: Sep. 25, 2018

(54) METHOD, APPARATUS, AND A SYSTEM FOR FACILITATING BENDING OF AN INSTRUMENT IN A SURGICAL OR MEDICAL ROBOTIC ENVIRONMENT

(71) Applicant: Auris Health, Inc., Redwood City, CA (US)

(72) Inventors: Enrique Romo, Dublin, CA (US); Travis Schuh, Los Altos, CA (US)

(73) Assignee: Auris Health, Inc., Redwood City, CA (US)

( * ) Notice: Subject to any disclaimer, the term of this patent is extended or adjusted under 35 U.S.C. 154(b) by 666 days.

(21) Appl. No.: 14/479,095

(22) Filed: Sep. 5, 2014

(65) Prior Publication Data

US 2014/0379000 A1    Dec. 25, 2014

Related U.S. Application Data

(63) Continuation-in-part of application No. 14/201,610, filed on Mar. 7, 2014.

(60) Provisional application No. 61/774,901, filed on Mar. 8, 2013.

(51) Int. Cl.
*A61B 17/29* (2006.01)
*A61B 34/00* (2016.01)
*A61B 34/30* (2016.01)
*A61B 17/00* (2006.01)
(Continued)

(52) U.S. Cl.
CPC .............. *A61B 17/29* (2013.01); *A61B 34/30* (2016.02); *A61B 34/71* (2016.02); *A61B 2017/00309* (2013.01); *A61B 2017/00845* (2013.01); *A61B 2017/00867* (2013.01); *A61B 2017/2902* (2013.01); *A61B 2017/2926* (2013.01); *A61B 2017/2937* (2013.01); *A61B 2034/306* (2016.02); *B25J 9/065* (2013.01); *B25J 9/104* (2013.01)

(58) Field of Classification Search
CPC ......... A61B 17/29; A61B 34/30; A61B 34/71; A61B 1/0055; A61B 1/0056; A61B 1/0057; A61B 17/00234; A61B 2017/00309; A61B 2017/2937; B25J 9/065; B25J 9/104
USPC ............... 74/490.04; 600/141, 142, 146, 153
See application file for complete search history.

(56) References Cited

U.S. PATENT DOCUMENTS

| | | |
|---|---|---|
| 3,572,325 A | 3/1971 | Bazell et al. |
| 4,580,551 A * | 4/1986 | Siegmund ............ A61B 1/0055 600/139 |
| 4,597,388 A | 7/1986 | Koziol et al. |

(Continued)

FOREIGN PATENT DOCUMENTS

| | | |
|---|---|---|
| CN | 1839764 A | 10/2006 |
| CN | 102088920 A | 6/2011 |

(Continued)

OTHER PUBLICATIONS

European search report and search opinion dated Sep. 16, 2016 for EP Application No. 14760802.0.

(Continued)

*Primary Examiner* — William C Joyce
(74) *Attorney, Agent, or Firm* — Knobbe, Martens, Olson & Bear, LLP

(57) ABSTRACT

An instrument that facilitates bending with large degrees of articulation while maintaining ease of manufacturing for medical and surgical applications is discussed.

18 Claims, 20 Drawing Sheets

(51) Int. Cl.
 B25J 9/10 (2006.01)
 B25J 9/06 (2006.01)

(56) References Cited

U.S. PATENT DOCUMENTS

| | | | |
|---|---|---|---|
| 4,700,693 A * | 10/1987 | Lia | A61B 1/0055 356/241.4 |
| 4,721,097 A * | 1/1988 | D'Amelio | A61B 1/0055 53/585 |
| 4,745,908 A | 5/1988 | Wardle | |
| 4,748,969 A | 6/1988 | Wardle | |
| 4,869,238 A | 9/1989 | Opie et al. | |
| 4,905,673 A | 3/1990 | Pimiskern | |
| 4,907,168 A | 3/1990 | Boggs | |
| 4,911,148 A * | 3/1990 | Sosnowski | A61B 1/0051 600/136 |
| 5,106,387 A | 4/1992 | Kittrell et al. | |
| 5,168,864 A | 12/1992 | Shockey | |
| 5,287,861 A | 2/1994 | Wilk | |
| 5,313,934 A | 5/1994 | Wiita et al. | |
| 5,381,782 A * | 1/1995 | DeLaRama | A61B 1/0056 138/118 |
| 5,425,735 A | 6/1995 | Rosen et al. | |
| 5,462,561 A * | 10/1995 | Voda | A61B 17/0057 112/169 |
| 5,472,406 A | 12/1995 | De La Torre et al. | |
| 5,477,856 A | 12/1995 | Lundquist | |
| 5,507,725 A | 4/1996 | Savage et al. | |
| 5,572,999 A | 11/1996 | Funda et al. | |
| 5,662,590 A | 9/1997 | De La Torre et al. | |
| 5,695,500 A | 12/1997 | Taylor et al. | |
| 5,704,534 A | 1/1998 | Huitema et al. | |
| 5,873,817 A | 2/1999 | Kokish et al. | |
| 5,876,325 A | 3/1999 | Mizuno et al. | |
| 5,910,129 A | 6/1999 | Koblish et al. | |
| 5,928,163 A * | 7/1999 | Roberts | A61B 10/06 600/567 |
| 6,012,494 A * | 1/2000 | Balazs | F16C 1/04 138/110 |
| 6,019,772 A | 2/2000 | Shefaram et al. | |
| 6,033,371 A | 3/2000 | Torre et al. | |
| 6,157,853 A | 12/2000 | Blume et al. | |
| 6,198,974 B1 | 3/2001 | Webster, Jr. | |
| 6,326,616 B1 | 12/2001 | Andrien et al. | |
| 6,398,792 B1 | 6/2002 | O'Connor | |
| 6,406,486 B1 | 6/2002 | De La Torre et al. | |
| 6,436,107 B1 | 8/2002 | Wang et al. | |
| 6,491,626 B1 | 12/2002 | Stone et al. | |
| 6,554,793 B1 | 4/2003 | Pauker et al. | |
| 6,638,246 B1 | 10/2003 | Naimark et al. | |
| 6,671,581 B2 | 12/2003 | Niemeyer et al. | |
| 6,716,178 B1 | 4/2004 | Kilpatrick et al. | |
| 6,736,784 B1 | 5/2004 | Menne et al. | |
| 6,763,259 B1 | 7/2004 | Hauger et al. | |
| 6,827,712 B2 | 12/2004 | Tovey et al. | |
| 6,932,824 B1 * | 8/2005 | Roop | A61B 17/0057 606/139 |
| 7,008,401 B2 | 3/2006 | Thompson et al. | |
| 7,087,061 B2 | 8/2006 | Chemenko et al. | |
| 7,130,700 B2 | 10/2006 | Gardeski et al. | |
| 7,344,528 B1 | 3/2008 | Tu et al. | |
| 7,351,193 B2 | 4/2008 | Forman et al. | |
| 7,725,214 B2 | 5/2010 | Diolaiti | |
| 7,883,475 B2 | 2/2011 | Dupont et al. | |
| 7,930,065 B2 | 4/2011 | Larkin et al. | |
| 7,967,799 B2 | 6/2011 | Boukhny | |
| 8,049,873 B2 | 11/2011 | Hauger et al. | |
| 8,052,636 B2 | 11/2011 | Moll et al. | |
| 8,224,484 B2 | 7/2012 | Swarup et al. | |
| 8,256,428 B2 * | 9/2012 | Hindricks | A61B 18/1492 128/898 |
| 8,292,827 B2 * | 10/2012 | Musbach | A61M 25/0054 600/585 |
| 8,414,564 B2 | 4/2013 | Goldshleger et al. | |
| 8,444,637 B2 | 5/2013 | Podmore et al. | |
| 8,498,691 B2 | 7/2013 | Moll et al. | |
| 8,515,215 B2 | 8/2013 | Younge et al. | |
| 8,518,024 B2 | 8/2013 | Williams et al. | |
| 8,602,031 B2 | 12/2013 | Reis et al. | |
| 8,720,448 B2 | 5/2014 | Reis et al. | |
| 8,821,477 B2 * | 9/2014 | Northrop | A61M 25/0013 600/139 |
| 8,827,947 B2 | 9/2014 | Bosman et al. | |
| 8,827,948 B2 | 9/2014 | Romo et al. | |
| 8,894,610 B2 | 11/2014 | MacNamara et al. | |
| 8,961,533 B2 | 2/2015 | Stahler et al. | |
| 9,186,046 B2 | 11/2015 | Ramamurthy et al. | |
| 9,204,933 B2 | 12/2015 | Reis et al. | |
| 9,254,123 B2 | 2/2016 | Alvarez et al. | |
| 9,408,669 B2 | 8/2016 | Kokish et al. | |
| 9,427,551 B2 | 8/2016 | Leeflang et al. | |
| 9,462,932 B2 * | 10/2016 | Ostrovsky | A61B 1/0055 |
| 9,504,604 B2 | 11/2016 | Alvarez | |
| 9,561,083 B2 | 2/2017 | Yu et al. | |
| 9,591,990 B2 | 3/2017 | Chen et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,788,910 B2 | 10/2017 | Schuh | |
| 9,818,681 B2 | 11/2017 | Machida et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 2003/0195664 A1 | 10/2003 | Nowlin et al. | |
| 2004/0015122 A1 | 1/2004 | Zhang et al. | |
| 2004/0030349 A1 | 2/2004 | Boukhny | |
| 2004/0059257 A1 | 3/2004 | Gaber | |
| 2004/0135733 A1 | 7/2004 | Chou et al. | |
| 2004/0138525 A1 | 7/2004 | Saadat et al. | |
| 2004/0138529 A1 * | 7/2004 | Wiltshire | A61B 1/0055 600/144 |
| 2005/0004515 A1 | 1/2005 | Hart et al. | |
| 2005/0070844 A1 | 3/2005 | Chow et al. | |
| 2005/0125005 A1 | 6/2005 | Fujikura | |
| 2005/0154262 A1 | 7/2005 | Banik et al. | |
| 2005/0159646 A1 | 7/2005 | Nordstrom et al. | |
| 2005/0197623 A1 * | 9/2005 | Leeflang | A61B 1/0055 604/95.04 |
| 2005/0272975 A1 | 12/2005 | McWeeney et al. | |
| 2006/0041188 A1 * | 2/2006 | Dirusso | A61B 1/0055 600/146 |
| 2006/0111692 A1 | 5/2006 | Hlavka et al. | |
| 2006/0173243 A1 * | 8/2006 | Watanabe | A61B 1/0055 600/141 |
| 2006/0276827 A1 | 12/2006 | Mitelberg et al. | |
| 2007/0032906 A1 | 2/2007 | Sutherland et al. | |
| 2007/0060879 A1 | 3/2007 | Weitzner et al. | |
| 2007/0135733 A1 | 6/2007 | Soukijp et al. | |
| 2007/0135763 A1 | 6/2007 | Musbach et al. | |
| 2007/0135803 A1 | 6/2007 | Belson | |
| 2007/0270645 A1 | 11/2007 | Ikeda | |
| 2007/0270679 A1 | 11/2007 | Nguyen et al. | |
| 2007/0282167 A1 | 12/2007 | Barenboym et al. | |
| 2007/0287886 A1 | 12/2007 | Saadat | |
| 2007/0299427 A1 | 12/2007 | Yeung et al. | |
| 2008/0051629 A1 | 2/2008 | Sugiyama et al. | |
| 2008/0064921 A1 * | 3/2008 | Larkin | A61B 1/00087 600/104 |
| 2008/0065103 A1 | 3/2008 | Cooper et al. | |
| 2008/0065109 A1 | 3/2008 | Larkin | |
| 2008/0097293 A1 | 4/2008 | Chin et al. | |
| 2008/0108869 A1 | 5/2008 | Sanders et al. | |
| 2008/0114341 A1 | 5/2008 | Thyzel | |
| 2008/0177285 A1 | 7/2008 | Brock et al. | |
| 2008/0187101 A1 | 8/2008 | Gertner | |
| 2008/0208001 A1 | 8/2008 | Hadani | |
| 2008/0212082 A1 | 9/2008 | Froggatt et al. | |
| 2008/0218770 A1 | 9/2008 | Moll et al. | |

(56) References Cited

U.S. PATENT DOCUMENTS

| | | |
|---|---|---|
| 2008/0228104 A1 | 9/2008 | Uber et al. |
| 2008/0249483 A1* | 10/2008 | Slenker ............... A61B 1/0055 604/275 |
| 2009/0099420 A1 | 4/2009 | Woodley et al. |
| 2009/0171271 A1 | 7/2009 | Webster et al. |
| 2009/0247880 A1 | 10/2009 | Naruse et al. |
| 2009/0248041 A1 | 10/2009 | Williams et al. |
| 2009/0248043 A1 | 10/2009 | Tierney et al. |
| 2009/0254083 A1 | 10/2009 | Wallace et al. |
| 2009/0262109 A1 | 10/2009 | Markowitz et al. |
| 2009/0264878 A1 | 10/2009 | Carmel et al. |
| 2009/0268015 A1 | 10/2009 | Scott et al. |
| 2009/0312768 A1 | 12/2009 | Hawkins et al. |
| 2009/0326322 A1 | 12/2009 | Diolaiti |
| 2010/0030023 A1 | 2/2010 | Yoshie |
| 2010/0036294 A1 | 2/2010 | Mantell et al. |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0228191 A1 | 9/2010 | Alvarez et al. |
| 2010/0331856 A1 | 12/2010 | Carlson et al. |
| 2011/0009779 A1 | 1/2011 | Romano et al. |
| 2011/0028887 A1 | 2/2011 | Fischer et al. |
| 2011/0040404 A1 | 2/2011 | Diolaiti et al. |
| 2011/0046441 A1 | 2/2011 | Wiltshire et al. |
| 2011/0071508 A1* | 3/2011 | Duval ............... A61B 1/00087 606/1 |
| 2011/0106102 A1 | 5/2011 | Balicki et al. |
| 2011/0130718 A1 | 6/2011 | Kidd et al. |
| 2011/0152880 A1 | 6/2011 | Alvarez et al. |
| 2011/0237888 A1 | 9/2011 | Matsushita |
| 2011/0261183 A1 | 10/2011 | Ma et al. |
| 2011/0306836 A1 | 12/2011 | Ohline et al. |
| 2012/0071894 A1 | 3/2012 | Tanner et al. |
| 2012/0136419 A1 | 5/2012 | Zarembo et al. |
| 2012/0138586 A1 | 6/2012 | Webster et al. |
| 2012/0143226 A1 | 6/2012 | Belson et al. |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0012276 A1 | 1/2014 | Alvarez |
| 2014/0046313 A1 | 2/2014 | Pederson et al. |
| 2014/0069437 A1 | 3/2014 | Reis et al. |
| 2014/0142591 A1 | 5/2014 | Alvarez et al. |
| 2014/0276391 A1 | 9/2014 | Yu |
| 2014/0276594 A1 | 9/2014 | Tanner et al. |
| 2014/0276939 A1 | 9/2014 | Kokish et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2015/0025539 A1 | 1/2015 | Alvarez et al. |
| 2015/0051592 A1 | 2/2015 | Kintz |
| 2015/0101442 A1 | 4/2015 | Romo |
| 2015/0119637 A1 | 4/2015 | Alvarez et al. |
| 2015/0119638 A1 | 4/2015 | Yu et al. |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0335480 A1 | 11/2015 | Alvarez et al. |
| 2016/0001038 A1 | 1/2016 | Romo et al. |
| 2016/0007881 A1 | 1/2016 | Wong et al. |
| 2016/0151122 A1 | 6/2016 | Alvarez et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0065364 A1 | 3/2017 | Schuh et al. |
| 2017/0065365 A1 | 3/2017 | Schuh |
| 2017/0100199 A1 | 4/2017 | Yu et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055589 A1 | 3/2018 | Joseph et al. |

FOREIGN PATENT DOCUMENTS

| | | |
|---|---|---|
| EP | 0 543 539 | 5/1993 |
| EP | 0 776 739 | 6/1997 |
| EP | 1 442 720 | 8/2004 |
| EP | 0 904 796 | 11/2004 |
| JP | H09224951 A | 9/1997 |
| JP | 2010-046384 | 3/2010 |
| JP | 2011-015992 | 1/2011 |
| WO | WO 92/14411 A1 | 9/1992 |
| WO | WO 00/67640 | 11/2000 |
| WO | WO-0105849 A1 | 1/2001 |
| WO | WO 02/074178 | 9/2002 |
| WO | WO 03/096871 A2 | 11/2003 |
| WO | WO 04/039273 | 5/2004 |
| WO | WO 2004/105849 A1 | 12/2004 |
| WO | WO 05/032637 | 4/2005 |
| WO | WO 05/081202 | 9/2005 |
| WO | WO 09/097461 | 6/2007 |
| WO | WO 08/067540 | 8/2008 |
| WO | WO 09/092059 | 7/2009 |
| WO | WO-2010081187 A1 | 7/2010 |
| WO | WO 10/088187 | 8/2010 |
| WO | WO 2011/161218 A1 | 12/2011 |
| WO | WO-2014138729 A1 | 9/2014 |
| WO | WO-2016037133 A1 | 3/2016 |

OTHER PUBLICATIONS

Office action dated Sep. 2, 2016 for U.S. Appl. No. 14/201,610.
Office action dated Feb. 3, 2017 for U.S. Appl. No. 14/201,610.
U.S. Appl. No. 14/196,953, filed Mar. 4, 2014, Alvarez et al.
U.S. Appl. No. 14/201,610, filed Mar. 7, 2014, Romo.
U.S. Appl. No. 14/301,871, filed Jun. 11, 2014, Alavarez et al.
U.S. Appl. No. 14/458,042, filed Aug. 12, 2014, Kintz.
U.S. Appl. No. 14/523,760, filed Oct. 24, 2014, Alzarez et al.
U.S. Appl. No. 62/037,520, filed Aug. 14, 2014, Yu.
Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
Effect of microsecond pulse length and tip shape on explosive, bubble formation of 2.78 iLtm Er,Cr;YSGG and 2.94 iLtm Er:YAG laser. Paper 8221-12, Proceedings of SPIE, vol. 8221 (Monday Jan. 23, 2013).
Ehlers, et al. Integration of a spectral domain optical coherence tomography system into a surgical microscope for intraoperative imaging. Investigative Ophthalmology and Visual Science 52.6. 2011; 3153-3159.
Hubschman. Robotic Eye Surgery: Past, Present, and Future. Journal of Computer Science and Systems Biology, 2012.

(56) References Cited

OTHER PUBLICATIONS

International search report and written opinion dated Mar. 29, 2013 for PCT/US2012/069540.
International search report and written opinion dated Nov. 7, 2014 for PCT Application No. US2014/041990.
International search report dated Jun. 16, 2014 for PCT/US2014/022424.
Office action dated Jun. 19, 2014 for U.S. Appl. No. 13/868,769.
Stoyanov. Surgical vision. Annals of Biomedical Engineering 40.2. 2012; 332-345. Published Oct. 20, 2011.
International search report and written opinion dated Dec. 4, 2015 for PCT Application No. PCT/US15/48688.
European search report and search opinion dated Jul. 2, 2015 for EP Application No. 12856685.8.
Office action dated May 21, 2015 for U.S. Appl. No. 13/711,440.
Office action dated Jun. 11, 2015 for U.S. Appl. No. 14/158,548.
U.S. Appl. No. 14/542,373, filed Nov. 14, 2014, Romo et al.
U.S. Appl. No. 14/542,387, filed Nov. 14, 2014, Bogusky et al.
U.S. Appl. No. 14/542,403, filed Nov. 14, 2014, Yu et al.
U.S. Appl. No. 14/542,429, filed Nov. 14, 2014, Romo et al.
Office action dated Oct. 7, 2014 for U.S. Appl. No. 13/711,440.
U.S. Appl. No. 14/578,082, filed Dec. 19, 2014, Alvarez et al.
U.S. Appl. No. 14/583,021, filed Dec. 24, 2014, Romo et al.
International search report and written opinion dated Jan. 27, 2015 for PCT Application No. US2014/062284.
Office action dated Aug. 4, 2017 for U.S. Appl. No. 14/201,610.
International Search Report dated Jun. 16, 2014 in PCT/US14/22424.

* cited by examiner

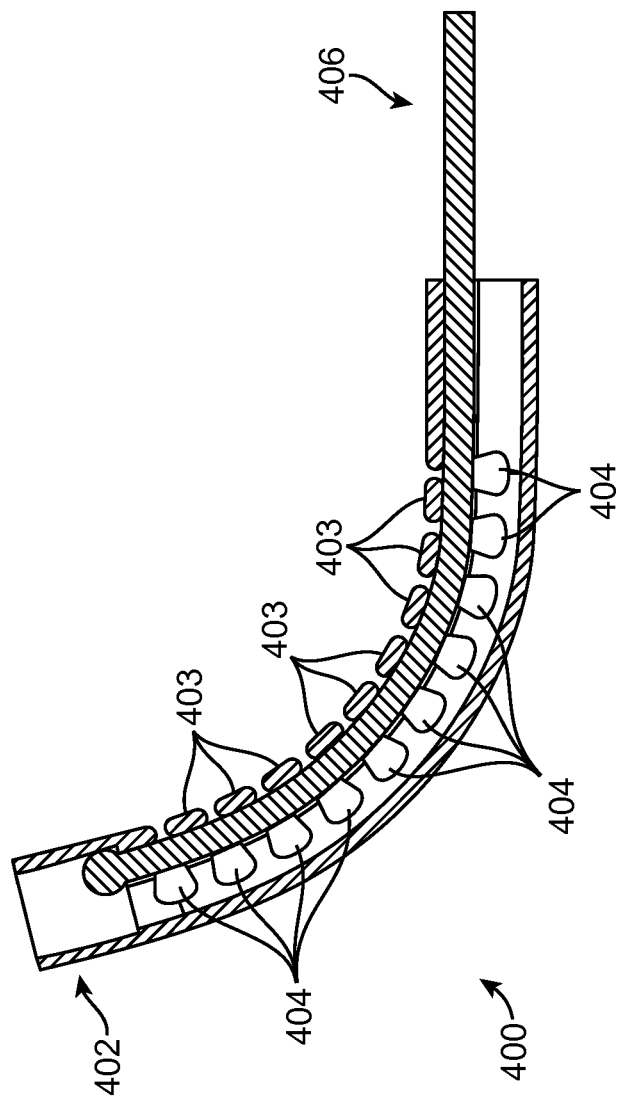

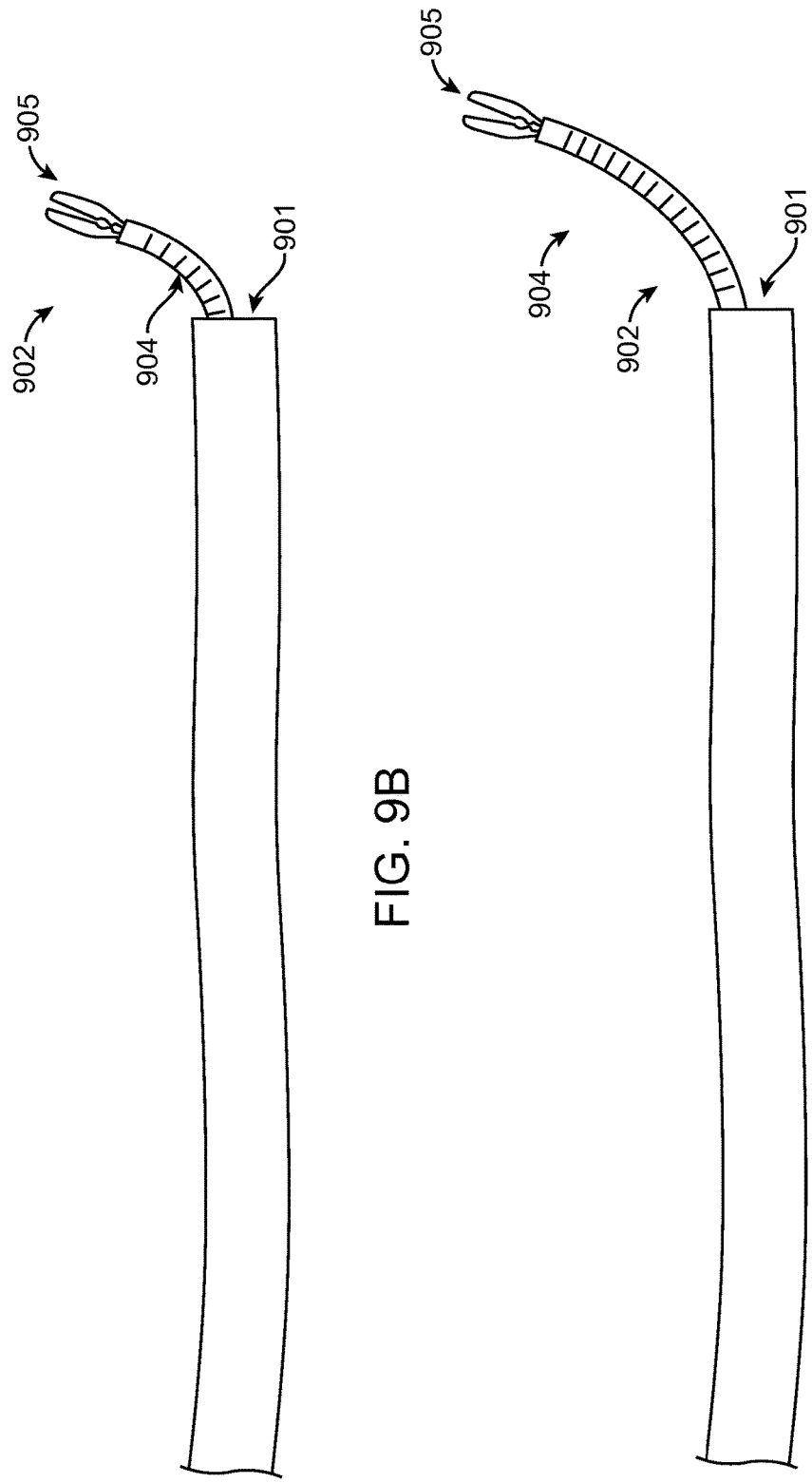

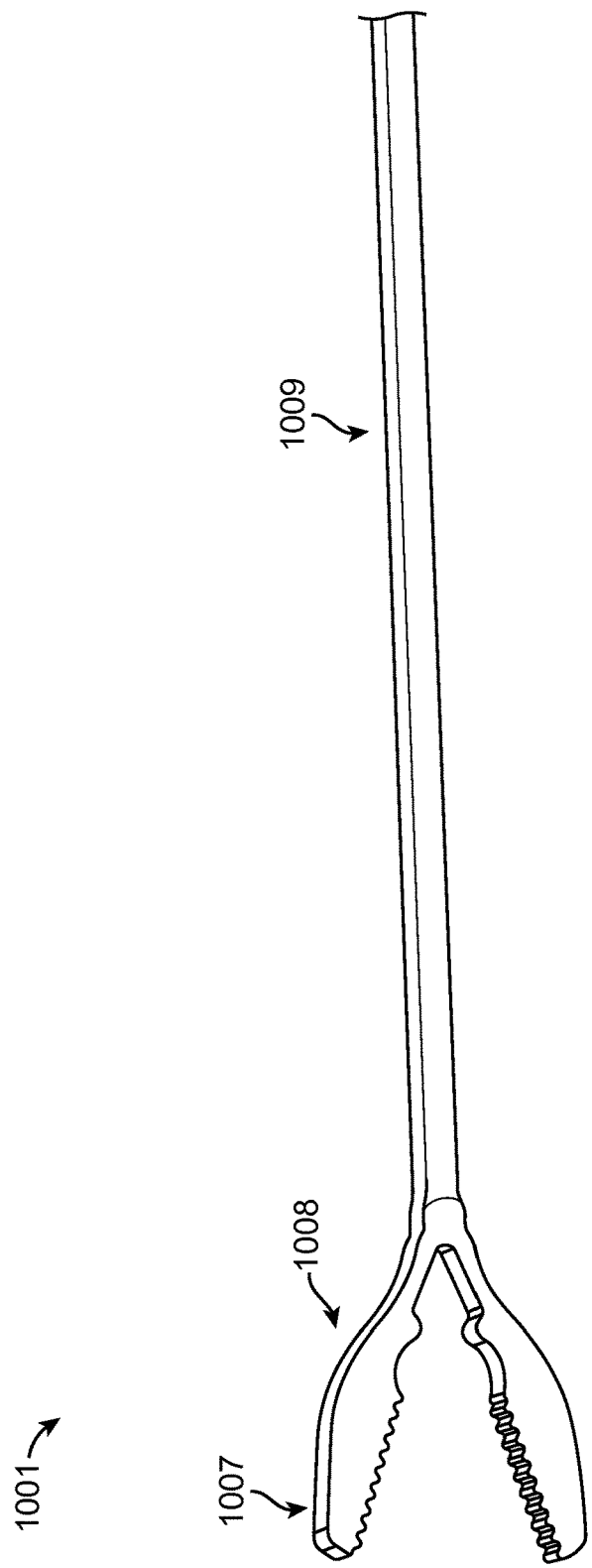

METHOD, APPARATUS, AND A SYSTEM FOR FACILITATING BENDING OF AN INSTRUMENT IN A SURGICAL OR MEDICAL ROBOTIC ENVIRONMENT

INCORPORATION BY REFERENCE AND CROSS-REFERENCE TO RELATED APPLICATIONS

This application is a continuation-in-part of U.S. application Ser. No. 14/201,610, filed Mar. 7, 2014, which claims priority to Provisional Application No. 61/774,901, filed Mar. 8, 2013, the entire contents of which are incorporated herein by reference.

BACKGROUND OF THE INVENTION

1. Field of the Invention

The field of the present application pertains to medical devices. More particularly, the field of the invention pertains to an apparatus, system, and method for performing surgery.

2. Description of the Related Art

Robotic surgery has many benefits to improve patient recovery time and allows precise control of medical and surgical application instruments. In robotics, an end effector is the device at the "end" of a robotic arm, designed to interact with the environment. As the end effector is the portion of a robot that interacts with the work environment, the exact nature of the end effector depends on the robot's application. For example, several examples of end effectors could include a set of forceps, a pair of scissors, a laser, a camera, a cautery tool, a needle, or any other instrument tip that would benefit from being able to be repositioned.

In the medical field, end effectors may have articulation capabilities that enable them to navigate through anatomical structures in order to reach the operative region. These articulating devices may have bending flexures that comprise a multitude of small moving parts. Typically, these devices present manufacture challenges due to the smaller geometries involved.

In addition to manufacturing challenges relating to the material of the bending flexures themselves, bending flexures in these articulable end effectors often contain a plethora of structures that enable a remote operator to perform the procedure, including pull wires, electrical wires, fluidic lines, and optical fibers. The presence of these components within the bending flexure also impact the device's performance and stability.

FIG. 1 illustrates how components within a bending flexure may be affected by bending moments in the bending flexure. In FIG. 1A, the bending flexure 100, comprising a proximal shaft 101 and distal articulation region 102, is unarticulated. Thus, bending flexure 100 remains perfectly straight, while pull wires 103 and 104 remain lax and of equal length. When unarticulated, bending flexure 100 remains concentric to the neutral axis 105 that runs longitudinally through the length of the bending flexure 100. When unarticulated, the path length of the pull wires 103 and 104 are of equal length within the distal bending flexure 102.

In FIG. 1B, the bending flexure 100 is articulated to the right. Accordingly, within the distal articulation region 102, the path length of pull wire 103 is extended to a distance represented by 106. In contrast, the path length of pull wire 104 is compressed to a distance represented by 107. As a result, the pull wires 103 and 104 exhibit uneven amounts of slack when exiting from the proximal shaft 101. The amount of extension and compression of the path length is proportional to its location relative to the neutral axis 105 in the bending flexure 100. As a rule, path lengths always elongate in the regions further from the direction of articulation, while shortening in paths closer to the direction of articulation.

Developing bending flexures for medical devices also raises a number of design challenges because the ideal articulable end effector is both stiff and bendable, depending on the scenario and required use. For example, when the physician is inserting and driving the end effector into a patient, the device must be relatively stiff in order for the device to pass through and around existing anatomical structures. However, when the physician needs to direct the distal end of the device to reach an operative region, the device is ideally very flexible and bendable. Balancing these design challenges is a constant obstacle for designers.

Existing solutions for bending flexures in small articulable instruments are manufactured using thin-walled tubes, such as hypotubes. Existing manufactures cut intricate patterns into the tubing in order to create reliefs that yield a preferential bending direction. If a large deflection is required; much of the tubing material is removed in order to allow for such bending. The resulting structure, however, is a thin-walled tube with a significant portion of material eliminated, which inevitably loses much of its structure and ability to remain mechanically stable. Especially when the outer diameter of the bending flexure is small, the walls of hypotube do not provide sufficient strength and rigidity when large degree articulations are required and where a surgical tool at the distal end requires rigidity to perform desired procedures.

Therefore, it would be advantageous to have a method and apparatus for facilitating the bending of an instrument with large degrees of articulation while maintaining a sufficient amount of stiffness in order to provide stability at the end effector, all while ensuring ease of manufacturing.

SUMMARY OF THE INVENTION

Embodiments described herein are directed to a method, apparatus, and system for bending of an instrument with large degrees of articulation while maintaining ease of manufacturing.

In one aspect, the present invention provides for a medical device that comprises an elongated body for use in medical procedures comprising a spine along the length of the elongated body; a series of ribs along the length of the elongated body, wherein the series of ribs form a corresponding series of ribbed voids along the length of the elongated body; and a non-cylindrical lumen longitudinally oriented within the elongated body, wherein the lumen has walls of uneven thickness formed from the elongated body.

In related devices, the spine is solid along the length of the elongated body. In some embodiments, the spine comprises a series of spinal ribs that form a series of corresponding spinal voids. In some embodiments, the ribs contain eyelets configured to convey an ancillary component along the length of the elongated body. In some embodiments, the ribbed voids are teardrop-shaped.

In related devices, the lumen is configured to convey an ancillary component along the length of the elongated body. In some embodiments, the present invention further comprises a forceps tool that is within the lumen. In some embodiments, the present invention further comprises a control wire that is configured to actuate an end effector that is operatively coupled to the control wire, wherein the control wire is positioned within the lumen proximal to the neutral axis of the elongated body. In some embodiments, the present invention further comprises a pull wire that is configured to articulate the elongated body. In some embodiments, the pull wire is positioned within the lumen and away from the neutral axis in order to maximize mechanical advantage. In some embodiments, the lumen comprises an upper region and a lower region. In some embodiments, the upper region of the lumen is proximal to the neutral axis and the lower region is away from the neutral axis. In some embodiments, the lumen is configured to convey a plurality of ancillary components.

In related devices, the present invention further comprises a shaft, comprising a distal end and proximal end, wherein the elongated body is aligned longitudinally within the shaft, and the elongated body is configured to extend from the distal end of the shaft.

In another aspect, the present invention provides for a method for performing medical procedures comprises directing an elongated tool towards an operative site, the tool comprising a proximal portion and distal portion; extending a longitudinally-aligned elongated body from the distal portion of the tool; articulating the elongated body towards the operative site; a series of ribs along the length of the elongated body, wherein the series of ribs form a corresponding series of voids along the length of the elongated body; and a non-cylindrical lumen longitudinally oriented within the elongated body, wherein the lumen has walls of uneven thickness formed from the elongated body.

In a related method, the tool is a flexible shaft. In some embodiments, the spine comprises a series of spinal ribs that form a series of corresponding spinal voids. In some embodiments, the lumen is configured to convey an ancillary component along the length of the elongated body.

In another aspect, the present invention provides for a medical device comprising an elongated body for use in medical procedures comprising a spine along the length of the elongated body; a series of ribs along the length of the elongated body, wherein the series of ribs form a corresponding series of voids along the length of the elongated body; and a plurality of lumens longitudinally oriented within the elongated body.

In a related device, the elongated body is cylindrical. In some embodiments, the spine is solid along the length of the elongated body. In some embodiments, the spine comprises a series of spinal ribs that form a series of corresponding spinal voids. In some embodiments, the ribs contain eyelets configured to convey an ancillary component along the length of the elongated body. In some embodiments, the voids are teardrop-shaped. In some embodiments, the lumens are each configured to convey an ancillary component along the length of the elongated body. In some embodiments, the device further comprises a forceps tool that is located within a lumen within the plurality of lumens that is proximal to the neutral axis of the elongated body. In some embodiments, the device further comprises a control wire that is located within a lumen in the plurality of lumens that is proximal to the neutral axis of the elongated body, and that is configured to actuate an end effector that is operatively coupled to the control wire. In some embodiments, the device further comprises a pull wire that is configured to articulate the elongated body and is located within a lumen in the plurality of lumens away from the neutral axis of the elongated body.

BRIEF DESCRIPTION OF THE DRAWINGS

The invention will be described, by way of example, and with reference to the accompanying diagrammatic drawings, in which:

FIGS. 4A-4C illustrate views of a flexible bending flexure in accordance with an embodiment of the present invention;

FIGS. 9A-9C illustrate views of an endoscopic device incorporating a distally-located tool, in accordance with an embodiment of the present invention; and FIGS. 10A-10B illustrates components that comprise an articulating tool, in accordance with an embodiment of the present invention.

DETAILED DESCRIPTION OF THE PREFERRED EMBODIMENT

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The embodiments described herein are directed to an apparatus for a distal bending flexure of minimally invasive surgical instrument having a large degree of articulation and providing sufficient rigidity to resolve the required forces during remote surgical procedures. Other embodiments provide methods of using the distal bending flexure and methods for making it.

Figure 1A:
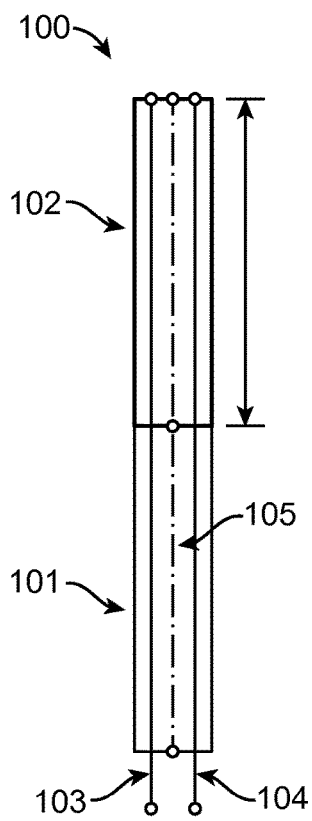
FIGS. 1A-1B illustrate how components within a bending flexure may be affected by bending moments.
Figure 1B:
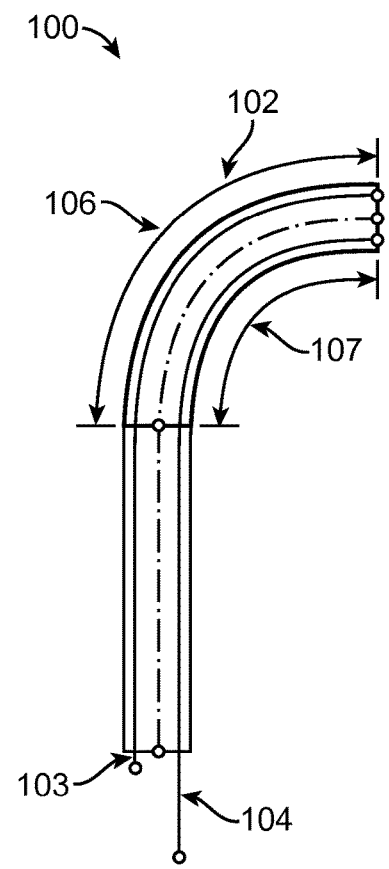
Figure 2A:
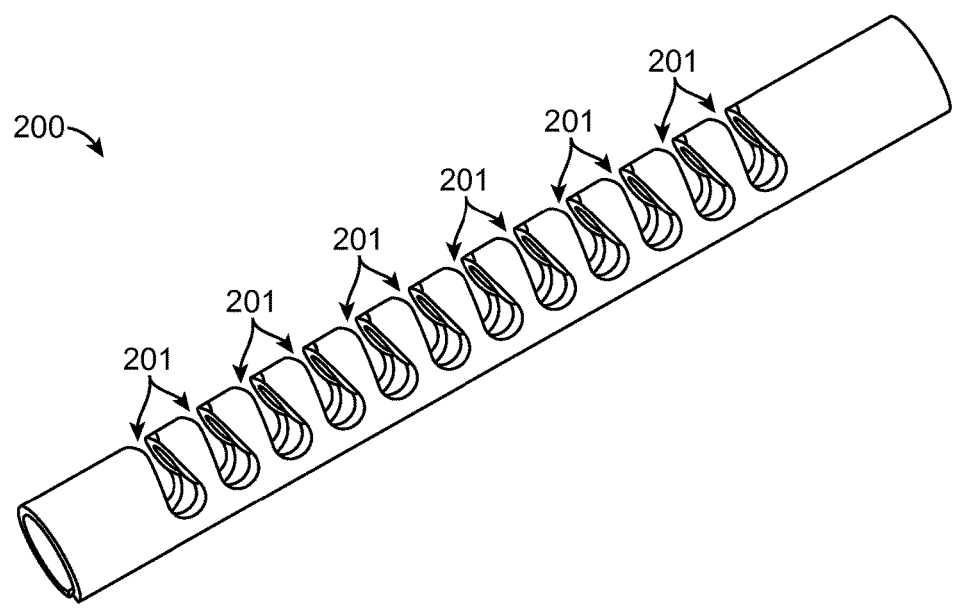
FIGS. 2A-2B illustrate external views of a flexible bending flexure in accordance with an embodiment of the present invention.
Figure 2B:
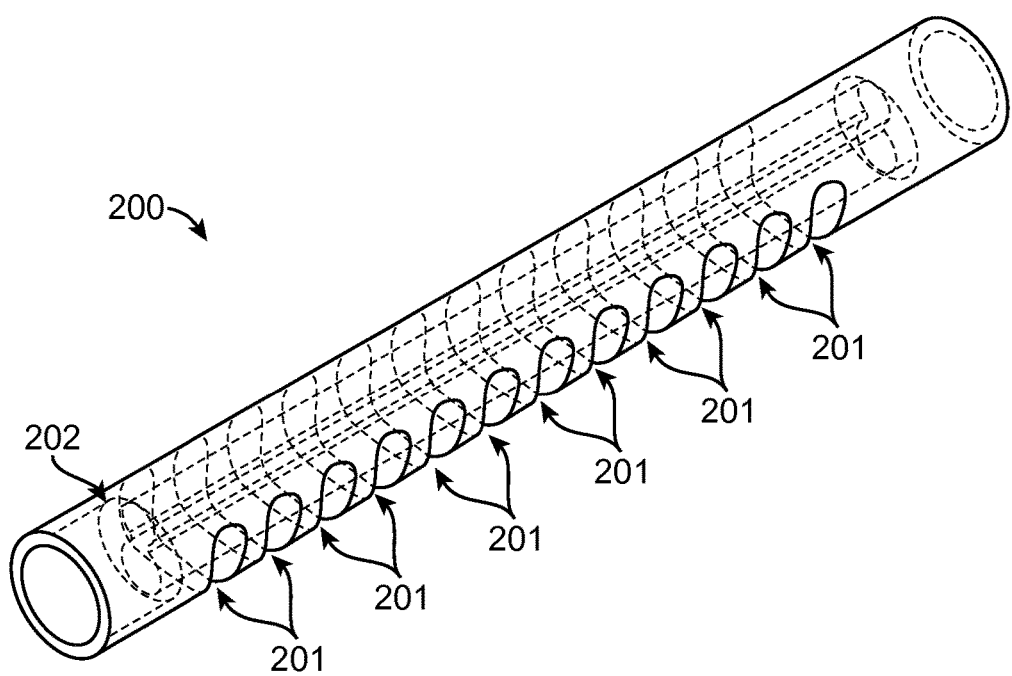

FIG. 2 illustrates external views of a flexible bending flexure in accordance with an embodiment of the present invention. In FIG. 2A, bending flexure 200 has material removed or "cut out" to create a series of voids 201 to reduce bending stiffness in the direction of voids 201. Additionally, the pattern of voids 201 allows for more predictable bend behavior. FIG. 2B illustrates an alternate view of a flexible bending flexure 200 where the external material is transparent. FIG. 2B clearly shows that the spine 202 of bending flexure 200, i.e., portion of the bending flexure 200 furthest from the intended bend direction, remains solid. The solid construction of the spine 202 helps to maintain the integrity of bending flexure 200. Skilled artisans would recognize that the length of the bending section, shapes of the voids and ribbing may be configured for bending flexure 200 to exhibit different properties.

In various embodiments, the "spine" of a flexure may be portion of the flexure that is opposite the direction of articulation, opposite the location of ribbing, or opposite location of any pull wires or articulation means.

Figure 3:
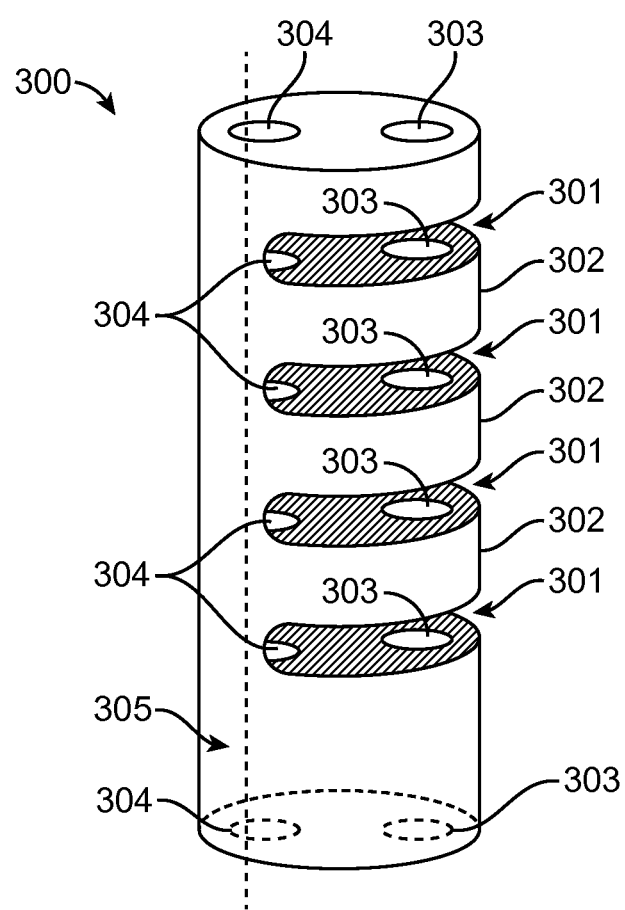
FIG. 3 illustrates a view of a flexible bending flexure in accordance with an embodiment of the present invention.

FIG. 3 illustrates a view of a flexible bending flexure in accordance with an embodiment of the present invention. In FIG. 3, bending flexure 300 has material removed or "cut out" to create a series of voids 301 to reduce bending stiffness in the direction of voids 301. Much like voids 201 from FIG. 2, the voids 301 in bending flexure 300 allow for more predictable bend behavior in the direction of the voids 301. The remaining material of bending flexure 300 also forms ribs 302, much like the ribs 203 of material in FIG. 2. In bending flexure 300, the ribs 302 may be used to convey a control lumen through extruded eyelets 303 that run through every single one of the ribs 301. A central lumen 304 that passes longitudinally through the solid portion of bending flexure 300 may be used for other purposes, such as a working channel for tools, a control lumen for a guidewire, or a control lumen for a grasper. A solid spine 305 in bending flexure 300 may be maintained to preserve the integrity and stiffness of the structure.

Figure 4A:
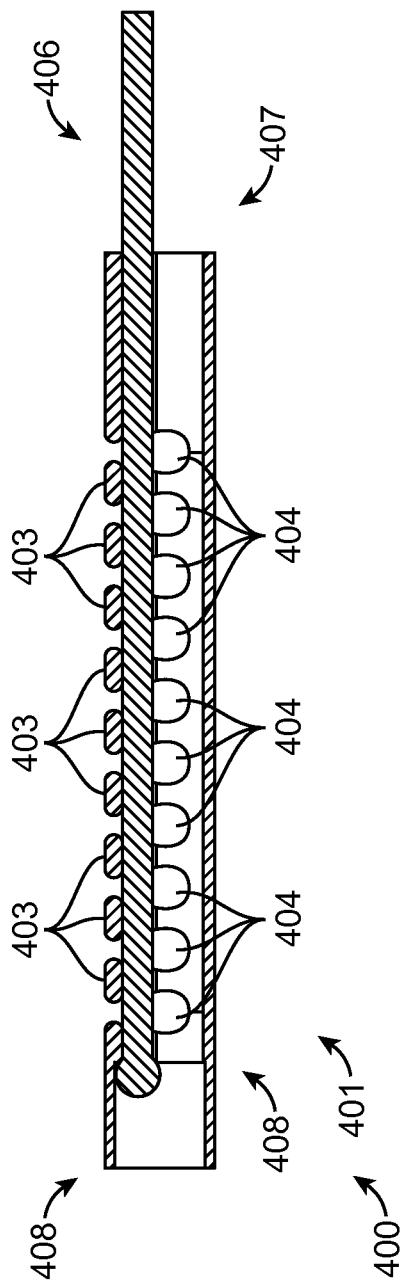

FIG. 4 illustrates views of a flexible bending flexure in accordance with an embodiment of the present invention. Specifically, FIG. 4A illustrates a flexible bending flexure 400 in an unarticulated position, in accordance with an embodiment of the present invention. In FIG. 4A, bending flexure 400 comprises a bending section 401, a solid spine 402, solid ribs 403, and voids 404 created by the removal of material. The ribs 403 also contain a series of concentric eyelets that may be used to convey a pull wire tendon 406 from the proximal end 407 of the bending flexure 400 to the distal end 408, where the tendon is fixedly coupled to the flexure 400.

FIG. 4B illustrates flexible bending flexure 400 in a slightly articulated position, in accordance with an embodiment of the present invention. As tensile forces are exerted on tendon 406 to "pull" it, the tendon 406 exerts compressive force on the top side of flexure 400, causing it to articulate towards the ribs 403 and voids 404. During articulation, the absence of material due to voids 404 relieves the compressive forces and allows for tighter articulation within material yield limit. The mechanical advantage of tendon 406 is enhanced during articulation the farther the tendon 406 exists from the neutral axis. Accordingly, some embodiments position tendons as far as possible from the neutral axis. In contrast, articulation results in extension forces on the spine 402 on the left side of the flexure 400 as the flexure 400 articulates to the right.

Figure 4C:
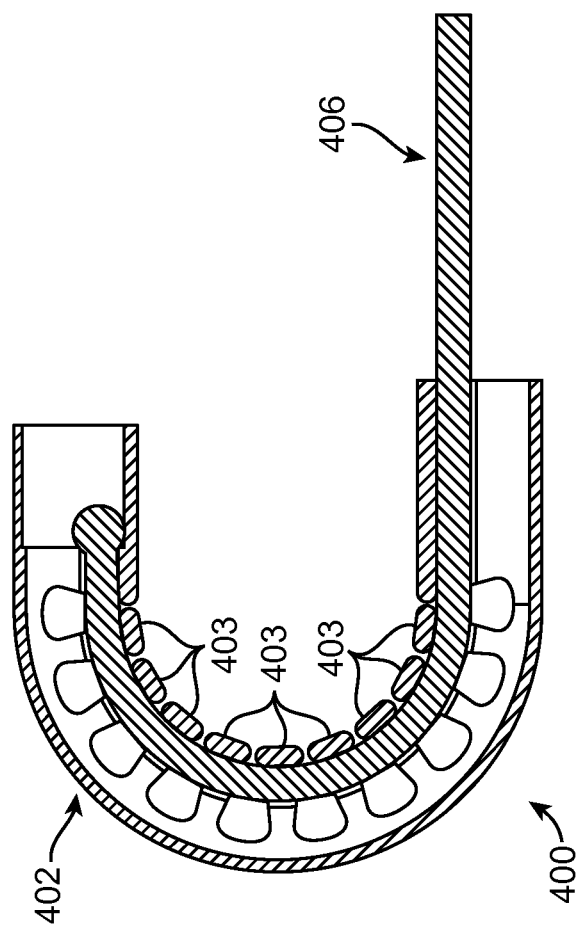

FIG. 4C illustrates flexible bending flexure 400 in a maximally articulated position, in accordance with an embodiment of the present invention. As additional tensile forces are exerted on tendon 406 to "pull" it, the compressive force on the right side of flexure 400 causes the flexure to dramatically bend to its right. In this position, the ribs 403 are touching each other, creating an effective "stop" to any further articulation. Articulation of this magnitude results in high extension stress/strain on the spine 402 on the left side of the flexure 400 as the flexure 400 articulates to the right.

Figure 5A:
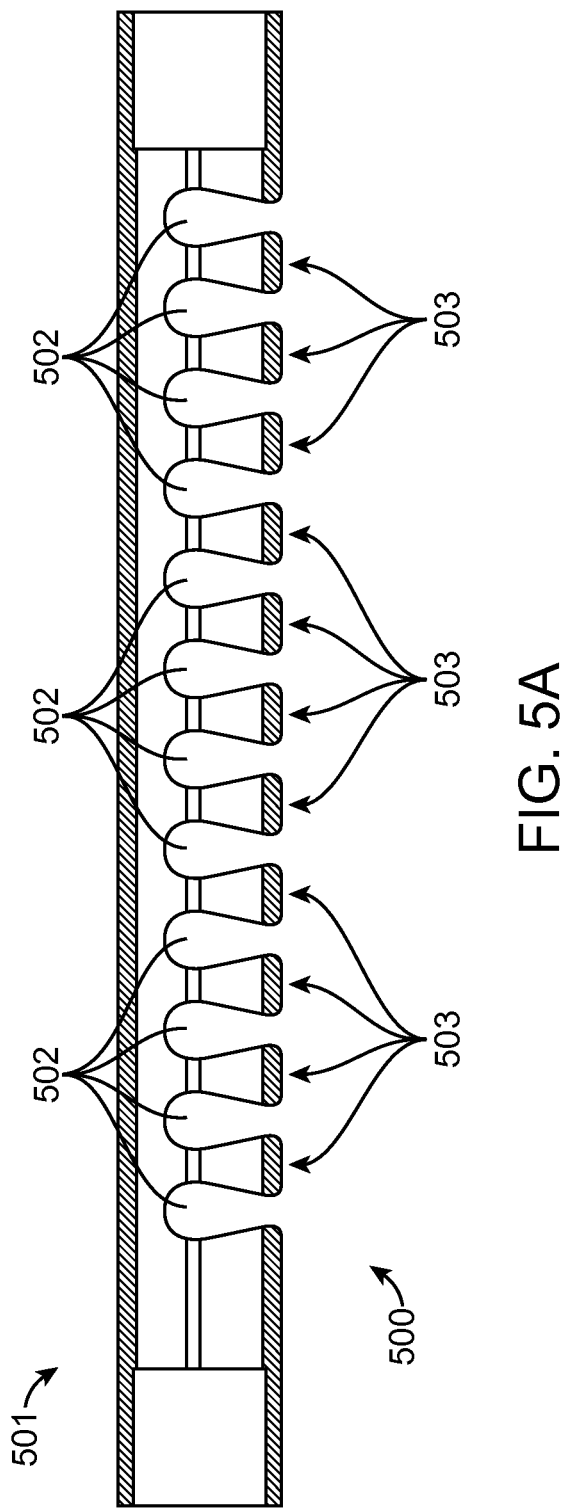
FIGS. 5A-5C illustrate various views of a bending flexure 500, in accordance with an embodiment of the present invention.

FIG. 5 illustrates various views of a bending flexure 500, in accordance with an embodiment of the present invention. Specifically, FIG. 5A illustrates longitudinally-cutout view of bending flexure 500 with a solid spine 501, voids 502 created by removing material, and ribs 503 formed by the remaining material. At the base of each rib (503), solid rib linkages connect ribs (503) from one side of the flexure 500 to the other. The teardrop-shape of voids 502 reduces the material of bending flexure 500 to improve bendability, thus distributing strain along the length of the flexure 500. Conversely, the teardrop-shape also maximizes the length of the rib linkages, which improves the integrity and creates a "hard stop" for the articulation of the bending flexure 500. Ribs 503 also support and house the components that are required to articulate the structure and manipulate the end effector, such as a pull wire in a control lumen. The skilled artisan would appreciate the selection of shapes for the teardrop voids 502 and ribs 503 as a matter of design choice, as well as the amount of material left to form spine 501.

Figure 5B:
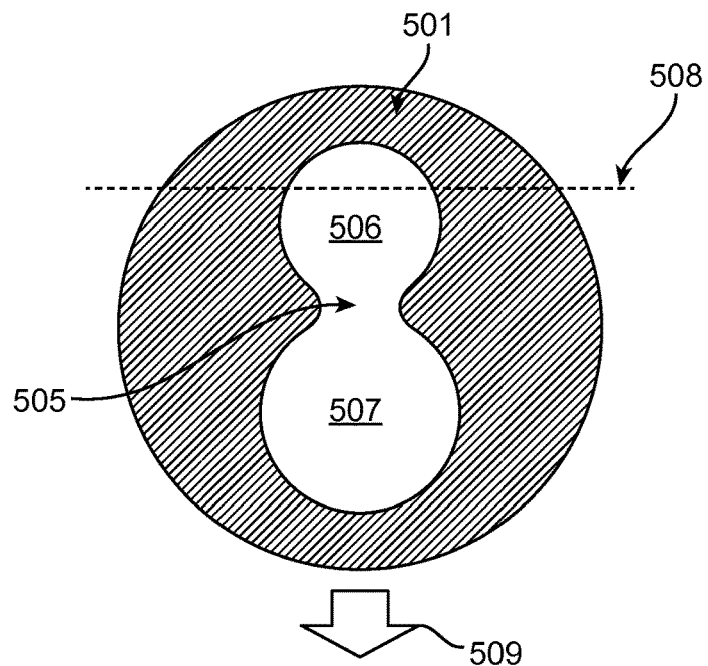

FIG. 5B illustrates a cross-sectional view of bending flexure 500, in accordance with an embodiment of the present invention. Specifically, FIG. 5B illustrates a cross-sectional view of a rib (503) from bending flexure 500, where a central lumen 505 runs down the length of bending flexure 500, allowing for components to pass through the flexure 500 for a variety of uses, such as a working channel for tools, a control lumen for a guidewire, or a control lumen for a grasper. In this embodiment, lumen 505 comprises an upper region 506 and lower region 507, each of which may accommodate a different tool or purpose. By design, the specific shape of the central lumen 505 provides room for components while also maximizing material in the bending flexure 500, providing rigidity and stiffness that enhances flexure integrity. A person of skill in the art would recognize that a variety of other lumen shapes to accommodate other purposes may be possible in bending flexure 500.

Figure 5C:
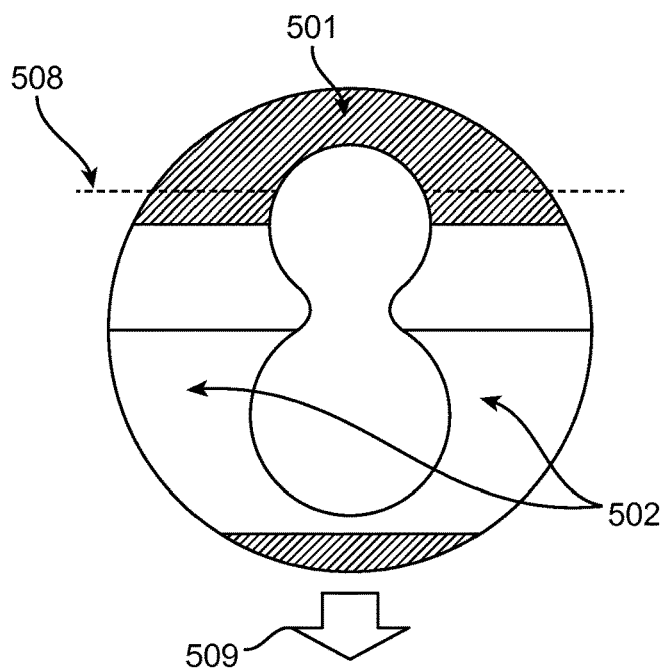

FIG. 5C illustrates a cross-sectional view of bending flexure 500, in accordance with an embodiment of the present invention. Specifically, FIG. 5C illustrates a cross-sectional view of a segment of bending flexure 500 with a void (502). As shown in FIG. 5C, even though the void creates open regions in flexure 500, the spine 501 of bending flexure 500, i.e., portion of the bending flexure 500 furthest from the intended bend direction, remains solid. While, the solid construction of the spine 501 helps to maintain the integrity of bending flexure 500, the removal of material to create the voids 502 reduces the compression strain on the direction of the bend, allowing for greater articulation in that direction.

In some embodiments, a tendon may be extended through the lower region 507 of lumen 505 and attached at the distal end of bending flexure 500. Referring back to FIG. 5A, when tension is applied to the tendon, bending flexure 500 will bend in a downward direction indicated by the arrow 509, because teardrop-shaped voids 502 permit ribs 503 to move inward, and a bend is realized along solid spine 501. Arrow 501 depicts the direction of the preferential bending away from the neutral axis in a downward direction. The skilled artisan would appreciate the selection of shapes for the teardrop voids 502 and ribs 503 as a matter of design choice, as well as the amount of material left to form spine 501.

Referring back to FIGS. 5B and 5C, due to the voids 502 in bending flexure 500, the neutral axis 508 of bending flexure 500 moves from the center of the bending flexure 500 towards the solid spine 501. It is this change in the physics of the bending flexure 500 that improves the bendability of the flexure 500. In some embodiments, the positioning of the lumens and their respective regions deliberately coincide with the location of the neutral axis 508 within bending flexure 500. For example, in certain embodiments, it may be advantageous to position a lumen or a region around the neutral axis for conveying a control wire for an end effector or a tool. In certain embodiments, it may be advantageous to position a lumen or a region away from the neutral axis to increase the mechanical advantage when articulating the flexure 500, such a pull wire.

Whereas existing solutions begin with a thin-walled tube, an alternative approach to manufacturing embodiments of the present invention include beginning with a solid cylindrical rod and removing material from the inside of the rod to create the appropriate lumens. This ensures that as much material remains in the bending flexure in order to provide structure and stiffness, while also providing the necessary space for required tools. The present invention may be the result of electro discharge machining cavities and voids out of a rod of solid material, such as nitinol. Alternatively, the material may be formed using extrusion techniques.

In some embodiments, the outer circumference of the bending flexure 500 has an approximately cylindrical shape, similar to that of a hypotube. Embodiments of the present invention provide a non-cylindrical lumen 505 through the bending flexure, which permits distributing material off-axis (i.e., non-uniform wall thickness) to provide structural rigidity to the bending flexure. Non-cylindrical lumen 505 provides a pathway 506 that may be used for the tools off-axis and a pathway 507 proximate to the neutral axis that may be used for auxiliary cables (not shown), such as tool actuating or articulating cables.

One embodiment provides placing the path of the ancillary components close to the neutral axis of the bending flexure. The placement reduces interactions between the articulation of the bending flexure and the ancillary components. This also contributes to a more predictable bend and end-effector behavior. In some embodiments, removing material from the cross section can both achieve a desired characteristic (e.g., bending stiffness of the bend section) and accommodate the articulation pull wire and the ancillary components.

In some embodiments, the bending flexure may be manufactured from a superelastic material. In other embodiments, the bending flexure is constructed from Nitinol, which has a superelastic phase at room and/or body temperature. In other embodiments, the bending flexure is constructed using other super elastic alloy, such as Nitinol tertiary alloys such as Ni—Ti—Co, Ni—Ti—Cu, and Ni—Ti—Fe.

In yet another embodiment, the moment of inertia may be tuned such that the structure achieves a significant bend by generating a moment on the structure and recovers to the original position when the moment is removed. In some embodiments, this actuation is accomplished by using a pull wire, which may be pulled in order to generate a moment and relaxed to relieve the moment.

In an alternative embodiment, the component is manufactured from a superplastic material, while the cross section allows a different inner profile by incorporating the relief on the profile, the device lends itself to be manufactured using the wire electric discharge machining (EDM) process without having to initially create a clearance hole.

One embodiment provides for placing the path of the ancillary components as close to the neutral axis of the bending flexure. Consequently, this reduces interactions between the articulation of the bending flexure and the ancillary components. Furthermore, this embodiment provides a more predictable bend and end effector behavior. For example, removing enough material from the cross section to accommodate the articulation pull wire and the ancillary components, hence, the bending stiffness can be manipulated in order to achieve a desired characteristic.

In certain embodiments, components that may be accommodated in the central lumen include pull wires for generating actuation at the end effector; fibers for illumination, laser, and vision; pneumatics and/or hydraulics; electrical wires; open lumen for a working channel (open architecture device, end effector is passed through working channel and is interchangeable); and a telescoping tube that supports an end effector.

In certain embodiments, the top opening, or lumen, accommodates the ancillary components and the bottom opening accommodates the articulating wire that controls the bending of the apparatus. A skilled artisan would appreciate different lumen configurations and placements based at least in part on the medical, surgical, or other application of the bending apparatus may be used without deviating from the present invention.

Figure 6A:
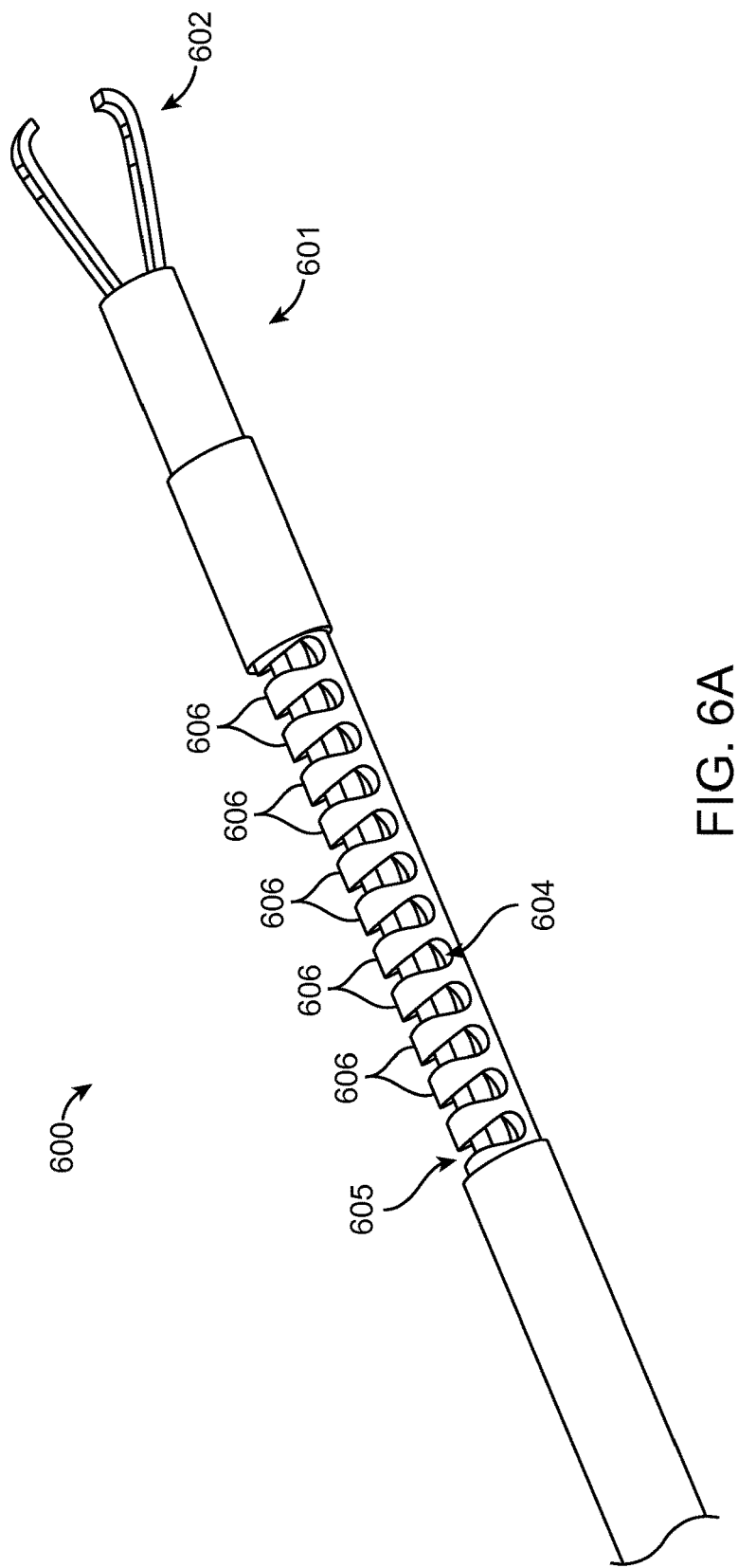
FIGS. 6A-6B illustrate aspects of a bend section incorporated into an end effector, according to an embodiment of the present invention.

FIG. 6 illustrates aspects of a bend section incorporated into an end effector, according to an embodiment of the present invention. Specifically, FIG. 6A illustrates an isometric view of a bend section 600 incorporated into an end effector interface 601 with an end effector that includes a grasper 602 at its distal end. Control over the grasper 602 is maintained by a pull wire 605 conveyed through the central lumen 604 of bend section 600. Articulation of bend section 600 may be controlled with pull wire 605 this is conveyed through eyelets in the ribs 606 of bending flexure 600.

Figure 6B:
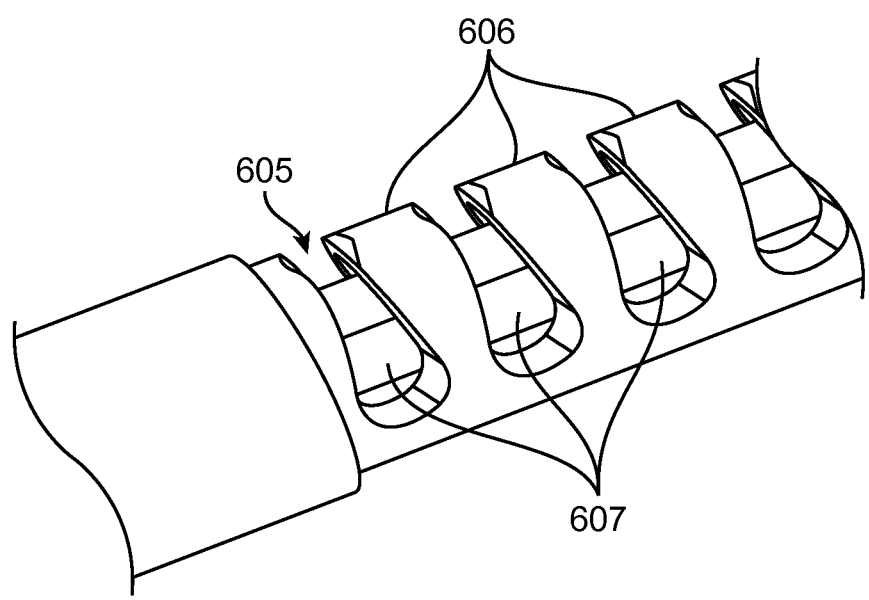

FIG. 6B illustrates a close-up isometric view of the bend section 600, in accordance with an embodiment of the present invention. Similar to embodiments disclosed earlier, the bend section 600 has teardrop-shaped voids 607 that improve articulation in a desired bending direction. Moreover, the presence of ribs 606 and voids 607 create a "hard stop" (a feedback of hitting a barrier) when the ribs 606 come in contact during articulation. Consequently, the ribs 606 and voids 607 help to prevent over articulation and potential damage to the structure of the bending flexure 600.

FIG. 7 illustrates aspects of a bending flexure in accordance with an embodiment of the present invention. Specifically, FIG. 7A illustrates an isometric view of a bending flexure in accordance with an embodiment of the present invention. In FIG. 7A, bending flexure 700 has material removed in order to create ribs 701 and voids 702, similar to the previously discussed embodiments. In addition, bending flexure 700 has a spinal gap 703 created by removing material from what was a solid spine in other embodiments. Even though FIG. 7A shows bending flexure 700 as a tubular elongated member with material removed to create ribs 701, voids 702, and a spinal gap 703, it would be appreciated that a similar structure could be created by removing material from a solid elongated tubular member in order to improve the stiffness, rigidity and structural integrity of the member.

The key difference in bending flexure 700 from FIG. 7 from previous embodiments is that the presence of spinal gap 703 reduces the extension strain resulting from an articulating motion towards the ribs 701 and voids 702. In practice, as the bending flexure 700 is articulated, the spinal gap 703 closes due to the extension strain, effectively holding the internal components in place, such as tools, pull wires, etc.

Figure 7A:
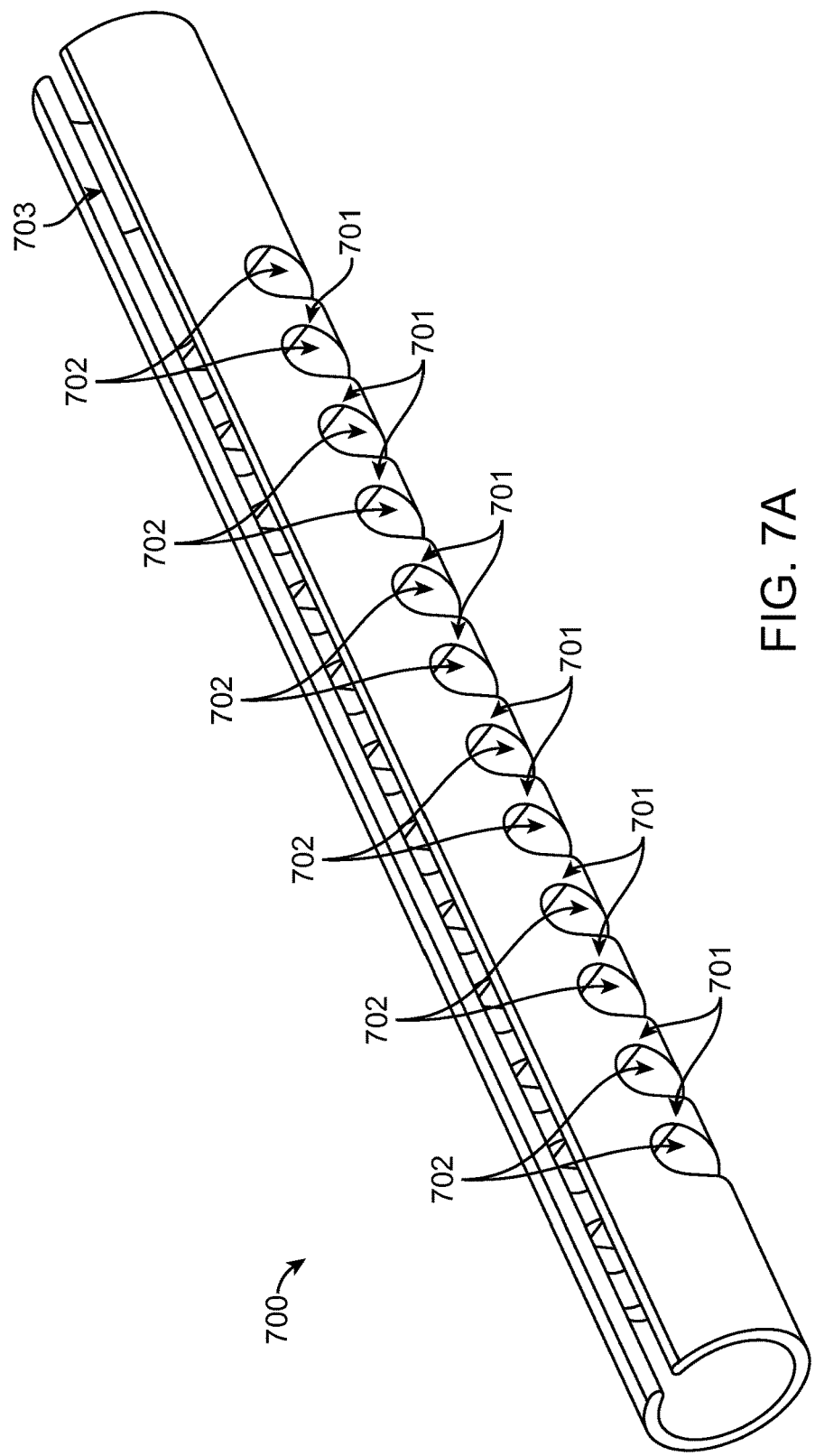
FIGS. 7A-7D illustrate aspects of a bending flexure in accordance with an embodiment of the present invention.
Figure 7B:
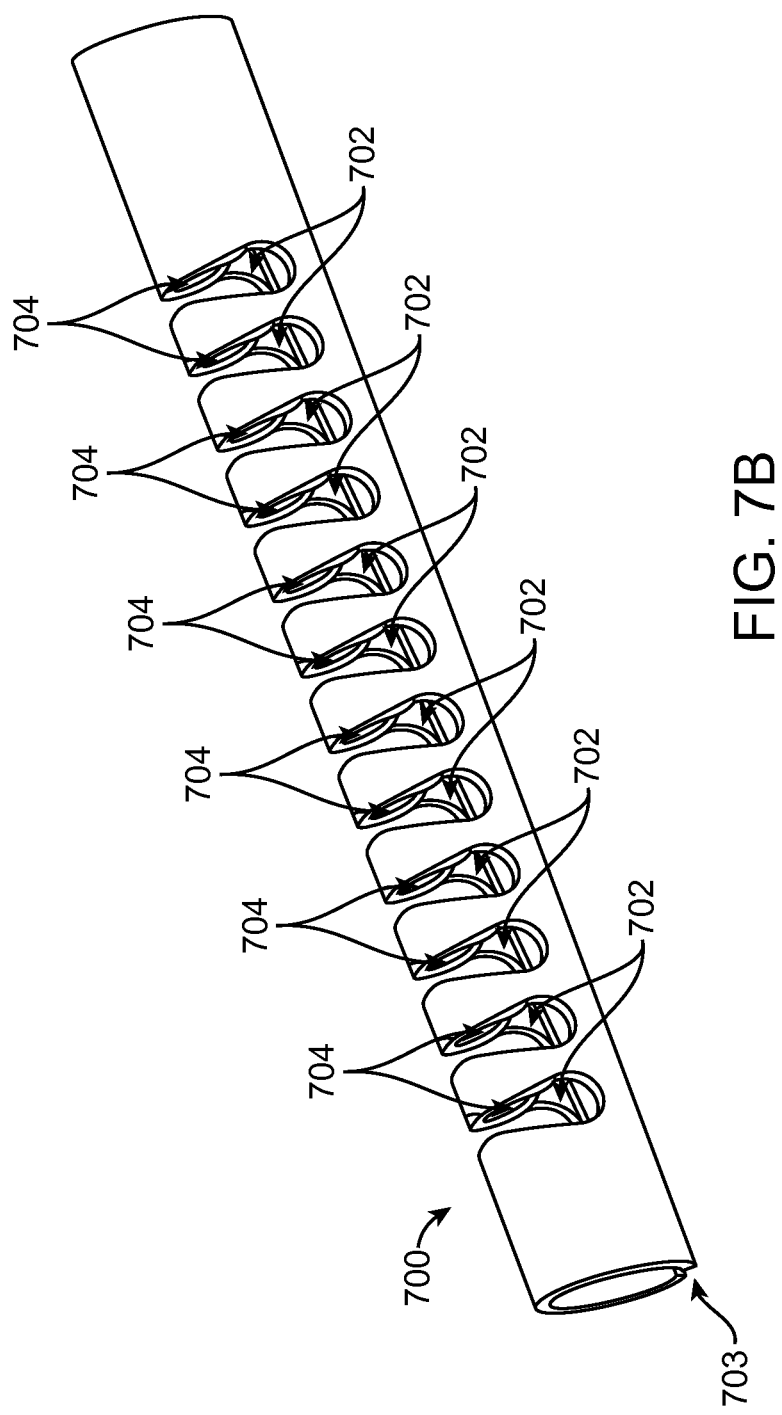

FIG. 7B illustrates a side view of the bending flexure 700 that highlights the structure of the ribs 701 and the shape of voids 702. As shown in FIG. 7B, voids 702 exhibit a teardrop-shape that resembles the void shapes in the previous embodiments. Additionally, the ribs 701 provide support for eyelets 704 that run the length of the bending flexure 700.

Figure 7C:
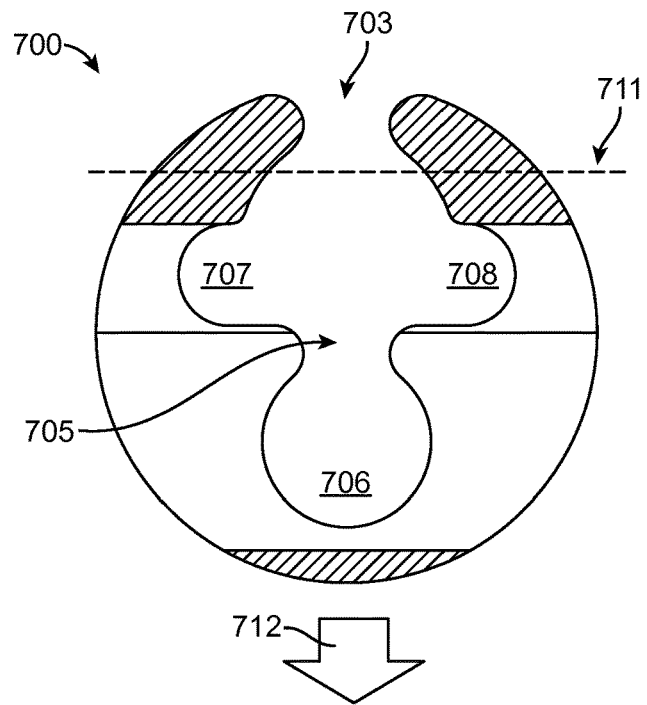

FIG. 7C illustrates a cross-sectional view of a segment of bending flexure 700 that coincides with a void (702), in accordance with an embodiment of the present invention. As shown in FIG. 7C, bending flexure 700 may have material removed to create a lumen 705 with accessible via the spinal gap 703. Lumen 705 may also be structured to provide for several subregions, lower region 706, left region 707, and right region 708, that may accommodate different tools and components, such as pull wires and cables or articulation, control wires for tools, and other ancillary components. As discussed earlier, the spinal gap 703 provides advantageous access to these components without having to rethread the components through the bending flexure. As with other embodiments, the bending flexure 700 is composed of solid material 709 outside of the lumen cut outs.

As shown in FIG. 7C, lumen 705 continues throughout bending flexure 700 such that lumen 705 is exposed due to the presence of a void (702). The presence of the void also moves the neutral axis 711 of the bending flexure 700 towards the spinal gap 703. As discussed earlier, during articulation in the direction of preferential bending 712, the spinal gap 703 will tend to close as the bending flexure 700 is articulated and will therefore minimize the possibility of having the ancillary components "escape" the inner profile lumens. During large articulations, the flexure will completely close. The spinal gap allows the structure to have lower bending stiffness and increases the ease of manufacturing.

Figure 7D:
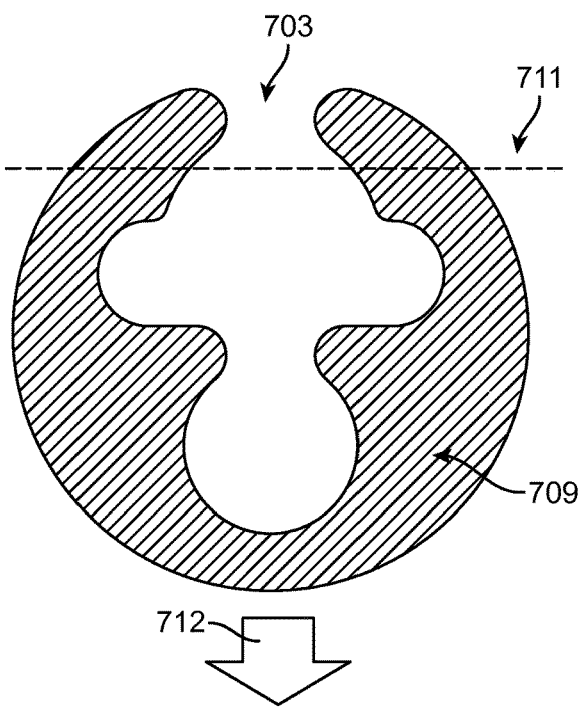

FIG. 7D illustrates a cross-sectional view of a segment of bending flexure 700 that coincides with a rib (701), in accordance with an embodiment of the present invention. As shown in FIG. 7D, the ribs are solid throughout the cross-section to provide structural integrity to flexure 700.

In some embodiments where the presence of the spinal gap 703 is a concern, the bending flexure can be manufactured with a gap and then "shape set" in order to close the gap before integration into an assembly. The skilled artisan would appreciate that the shape of non-cylindrical lumen 705 can be varied to achieve desired bending and rigidity properties of the bending flexure. The cross section of the design depicted in FIGS. 7C and 7D permit the inner profile to break out. By incorporating this relief on the profile, the device lends itself to be manufactured using the wire EDM process without having to initially create a clearance hole.

The presence of the spinal gap also has a benefit during the assembly process. Using the spinal gap, components, such as articulation/pull wires and ancillary components may be laterally, rather than axially, inserted into bending flexure 700. In cases of emergency, this capability allows bending flexure 700 to be replaced without having to sever the articulation/pull wires or any components.

Figure 8:
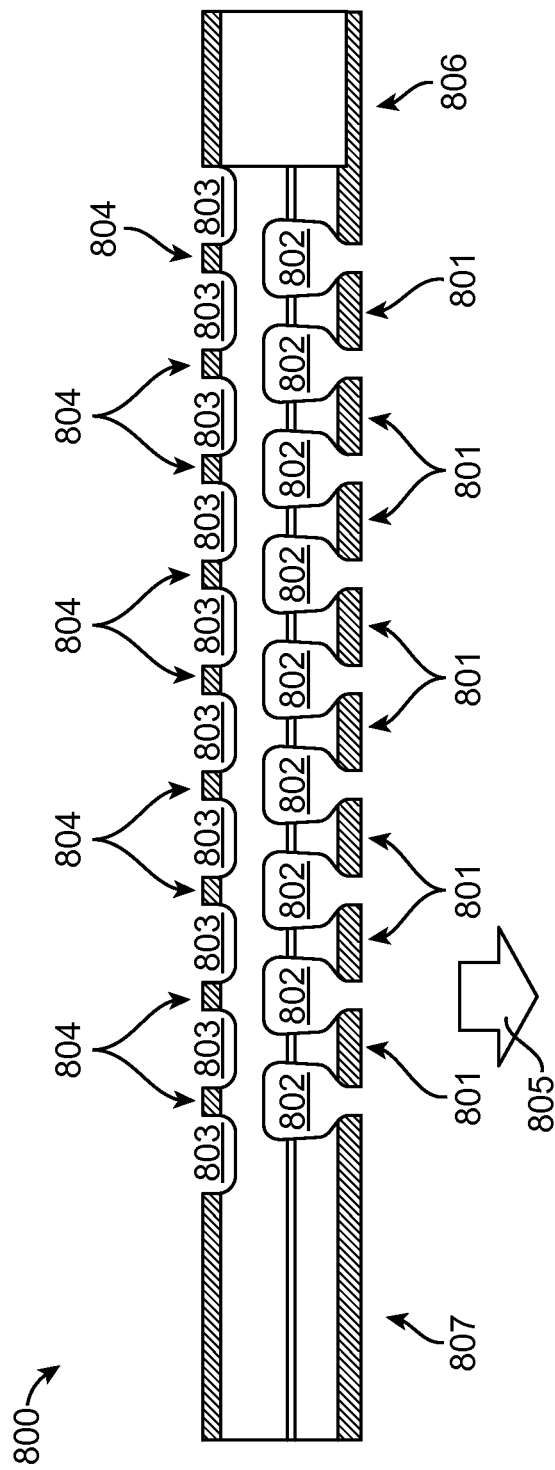
FIG. 8 illustrates a side view of a flexible bending flexure in accordance with an embodiment of the present invention.

FIG. 8 illustrates a side view of a flexible bending flexure in accordance with an embodiment of the present invention. While bending flexure 800 exhibits ribbing 801 and teardrop-shaped voids 802 consistent with previously-discussed embodiments, flexure 800 does not feature a solid spine or a longitudinally-oriented spinal gap. Instead, flexure 800 features a series of spinal voids 803 and spinal ribs 804 that minimize the extension forces on the spine of flexure 800 when articulation occurs in the direction 805 of the ribbing 801 and voids 802. In contrast to this embodiment, bending flexure 800 does not have extreme points of extension stress along its spine due to the spinal voids 804. Consistent with other embodiments, flexure may also exhibit solid ribbing joints and a proximal end 806 and distal end 807 where installed pull lumens may termination and be fixed coupled.

In some embodiments, the ribs may have gradations of thickness that may provide for a more consistent bend, and compensate for friction between pull wires in the lumen and the associated eyelets and/cavities that convey them down the length of the tool.

Use of the present invention may greatly enhance endoscopic procedures by providing dexterity at an endoscope's distal tip in order to perform various tasks, such as precise dissection and therapy delivery. Embodiments of the present invention may be delivered down the working channel of an endoscope, and its design allow it to be mounted on a flexible shaft.

Figure 9A:
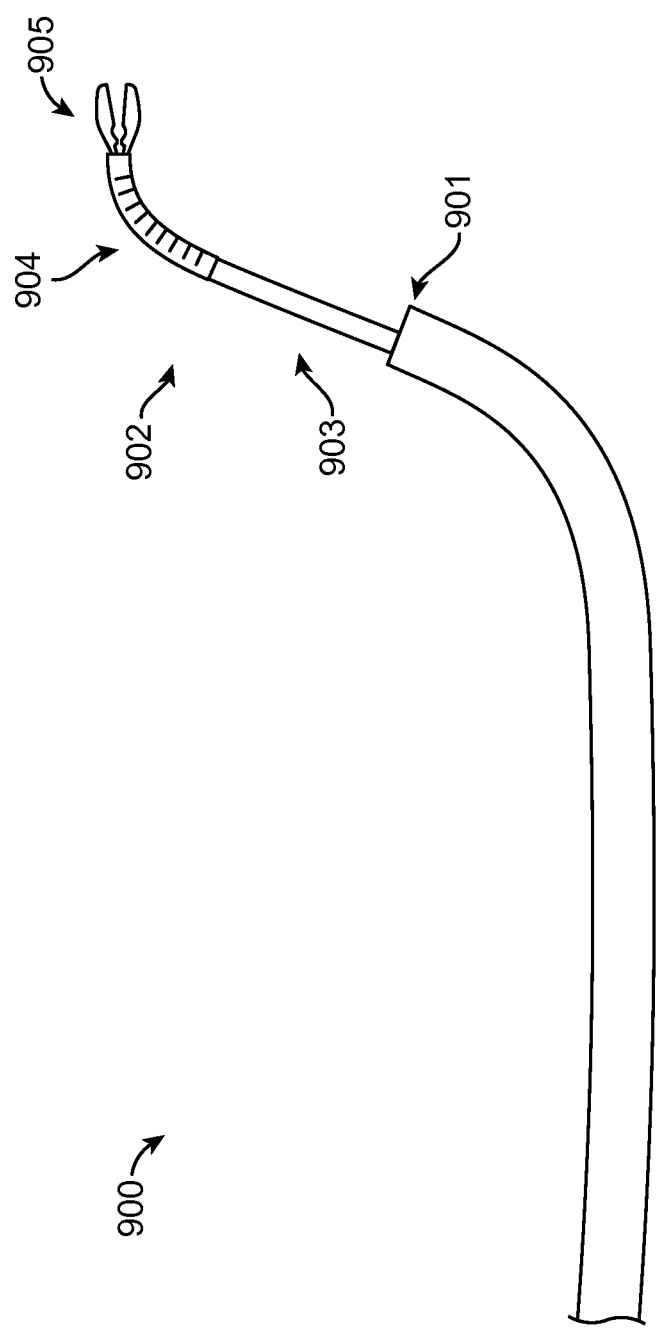

FIG. 9 illustrates views of an endoscopic device incorporating a distally-located tool, in accordance with an embodiment of the present invention. In FIG. 9A, a tool 902 may be concentrically positioned within an endoscopic device 900 for extension beyond the distal tip 901 of endoscopic device 900. In some embodiments, the endoscopic device 900 may be flexible and steerable. In some embodiments, the endoscopic device 900 may be steerable robotically. In some embodiments, the endoscopic device 900 may be constructed using catheter-like methods.

The tool 902 may comprise a flexible shaft 903, a bending flexure 904, and an effector, such as forceps 905. In certain embodiments, the shaft 903 may be rolled within endoscopic device 900 and articulated independent of endoscopic device 900. In some embodiments, the shaft 903 may be extended a predetermined length from the distal end 901 of the endoscopic device 900. In some embodiments, the shaft may be constructed from coil pipes or metal-braided shafts. In some embodiments, the end effector may be a laser fiber or biopsy needle. Moreover, the end effector (such as forceps 905) may be rolled and rotated as well.

The shaft may also be used to route wires for articulation of the bending flexure 904 and the actuation of the forceps 905, where the torqueability of the forceps 905 may be inversely proportional to the length of endoscopic device 900 and tool 902. Pull wires in these embodiments may be constructed from nitinol to take advantage of both its "memory" and superelastic properties under different conditions. Responsiveness of nitinol pull wires may be increased by increasing pull wire axial stiffness through transitioning from nitinol to a stiffer material, such as stainless steel, or braided cable, or torque tube in the case of controlling forceps.

In some embodiments, multiple aspects of the endoscopic device 900, flexible shaft 903, and bending flexure 904 may be adjusted and manipulated in order to reach different operative regions. For example, to reach deeper into a patient, the endoscopic device 900 may be extended, retracted, rolled or articulated in several directions. Similarly, flexible shaft 903 may be extended from or retracted from endoscopic device 900. At the same time, flexure 904 may be rolled and articulated while endoscopic device 900 and shaft 903 are also being adjusted, allowing for access variety of different operative regions.

FIG. 9B illustrates a side view of an endoscopic device incorporating distally-located tool 902, which comprises flexible shaft 903 and bending flexure 904, in accordance with an embodiment of the present invention. In FIG. 9B, the shaft 903 has been retracted, allowing articulation of bending flexure 904 almost immediately from the distal end 901 of endoscopic device 900.

FIG. 9C illustrates a side view of an endoscopic device incorporating distally-located tool 902, which comprises flexible shaft 903 and bending flexure 904, in accordance with an embodiment of the present invention. In FIG. 9C, the bending flexure 904 is extended to greater extent than in FIG. 9C, allowing access to articulation of bending flexure 904 to reach operative regions further away from the distal end 901 of endoscopic device 900. In some embodiments, the bending flexure 904 may be shape-set to curve in a predetermined direction, such that extension of flexure 904 from the distal tip 901 of endoscopic device 900 results in increased reach in the direction of the shape-set curve.

When deployed through a flexible endoscopic device, such as 900, a flexible shaft 903, and a flexible bending flexure, such as 904, the end effector may have as six degrees of articulation when accounting for both articulation and roll capabilities of the various components. However, where constrained, less than six degrees of articulation will result.

Figure 10A:
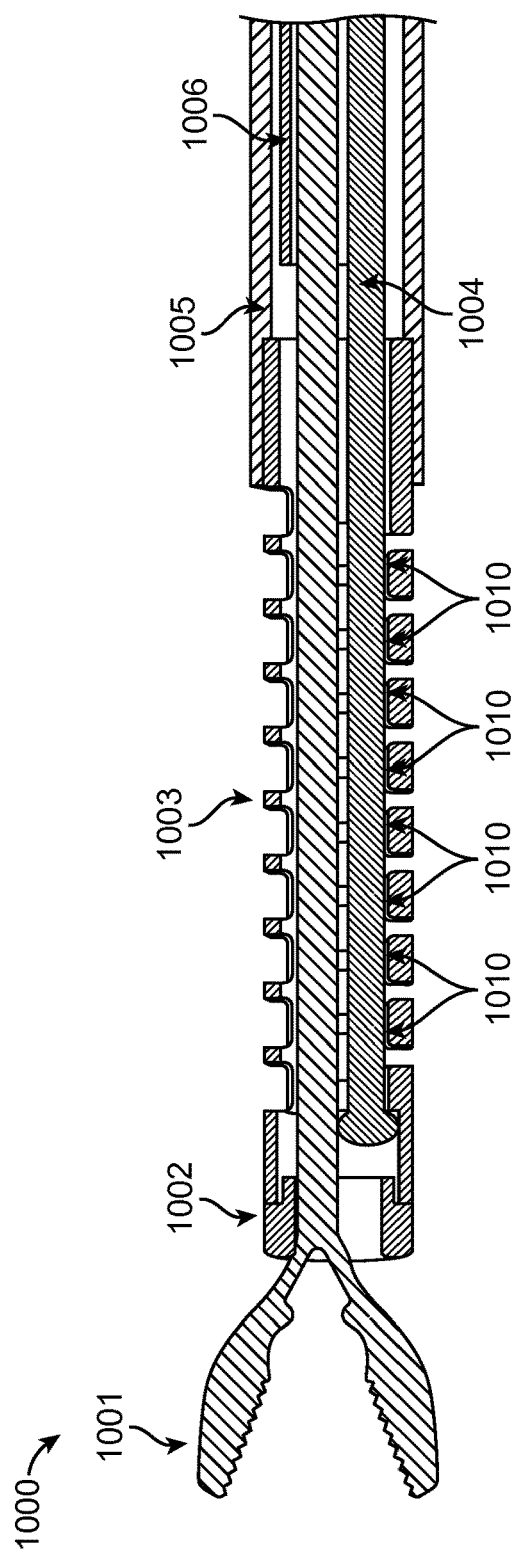

FIG. 10 illustrates components that comprise an articulating tool, in accordance with an embodiment of the present invention. FIG. 10A specifically illustrates a cutout side view of an articulating tool 1000 that comprises a forceps 1001, a bushing 1002, a bending flexure 1003, a pull wire 1004, a shaft 1005, and a stainless steel tube 1006. In some embodiments, the shaft may be flexible.

FIG. 10B illustrates a side view of the forceps 1001 from FIG. 10A, in accordance with an embodiment of the present invention. As shown in FIG. 10B, forceps grasper-rod 1001 comprises a grasper 1007 with prongs 1008 and transmission rod 1009. In some embodiments, the grasper 1007 and transmission rod 1009 may be constructed from nitinol in order to take advantage of its high strainability and stiffness. In certain instances, both components may be formed using a unibody construction in order to simplify the design and increase robustness. Moreover, nitinol's high strain limits allows the transmission rod 1009 a larger diameter, which increases torque transmission as torsional stiffness of an elongated member scales with the diameter of the member. In some embodiments, a stainless steel tube 1006 may be coupled to the transmission rod 1009 in order to improve torsional rigidity.

Returning to FIG. 10B, forceps 1001 may be retracted or extended within articulating tool 1000, through lumens in the bushing 1002, the bending flexure 1003, and shaft 1005. In an "open" state, the width of the prongs 1008 of grasper 1007 exceeds the diameter of the bushing 1002, thus retracting forceps 1001 into the articulating tool 1000 "closes" the prongs. Conversely, extending the forceps 1001 out of the bushing 1002 "opens" the prongs 1008 of grasper 1007. This simple means of (open-close) actuation greatly simplifies the tool, which is particular important at smaller geometries.

The bushing 1002 may be formed from hard materials and may include a low friction coating. In some embodiments, the bushing 1002 is formed from stainless steel or sapphire for their hardness properties. In certain embodiments, the bushing has a radiused edge to increase smoothness and reduce friction where the bushing rubs against the prongs 1008.

The bending flexure 1003 contains ribbing and voids consistent with earlier-discussed embodiments. Additionally, a pull wire 1004, running through concentric eyelets 1010 in the ribbing, may be used to articulate the bending flexure 1003 in the direction of the ribbing and voids. In certain embodiments, the transmission rod 1009 may be coated with a low friction coating, such as polytetrafluoroethylene (PTFE), to reduce friction between the transmission rod 1009 and the bending flexure 1003. In some embodiments, the interior of the bending flexure 1003 may be smoothed with an electropolish to reduce friction with the transmission rod 1009.

While contemplated for a range of sizes, the preferred embodiments of the present invention may be below 2 millimeters in diameter. In particular, embodiments are particularly useful for delivering rigidity and stability in miniature devices with sub-1 millimeter diameters.

Figure 11:
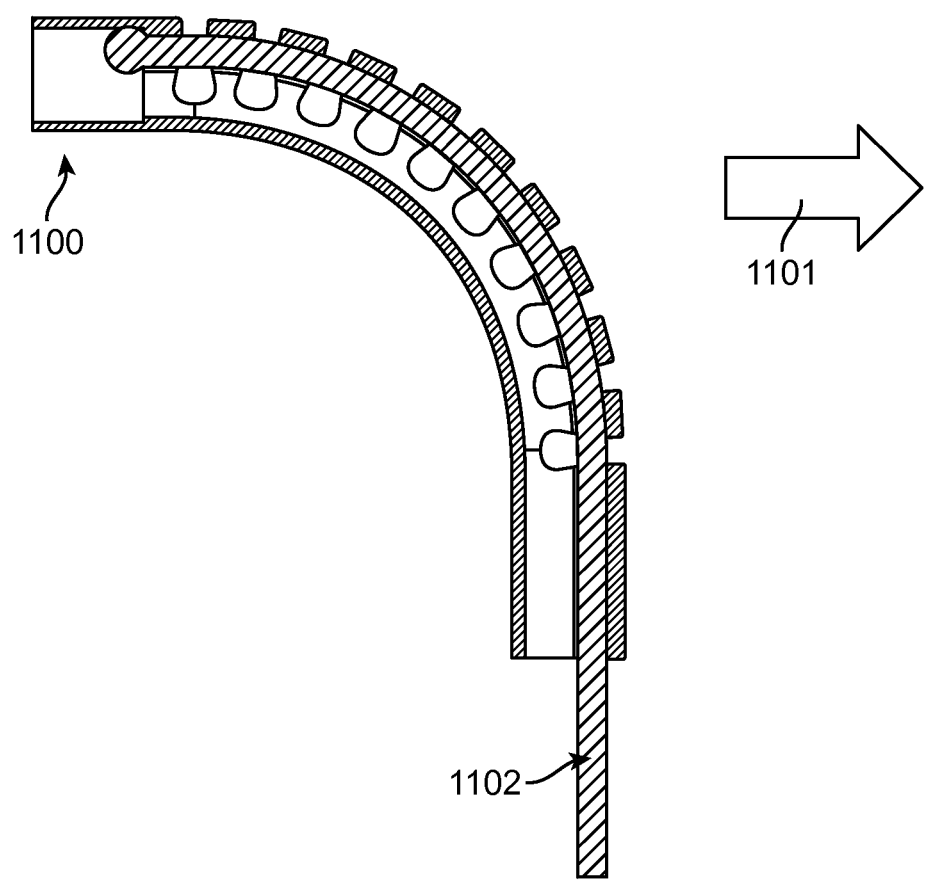
FIG. 11 illustrates a flexure that has been shape-set to be curved when relaxed, in accordance with an embodiment of the present invention.

While previously disclosed embodiments have included the use of approximately straight flexures when unarticulated, in some embodiments, the flexures of the present invention may be shape set to be non-straight as well. For example, FIG. 11 illustrates a flexure that has been shape-set to be curved to one side when relaxed, in accordance with an embodiment of the present invention. While flexure 1100 in FIG. 11 is identical in structure to flexure 400 in FIG. 4, flexure 1100 has been shape-set to be curved away from the direction of articulation 1101. This allows the flexure 1100 to reach a range of 180 degrees of motion rather than simply 90 degrees. For example, while flexure 1100 may reach operative regions to the left when the tendon 1102 is relaxed, flexure 1100 may reach operative regions in front of flexure 1100 and operative regions to the right upon tensioning tendon 1102.

Shape-setting allows the flexure to have additional degrees of freedom and reach. In some embodiments, a shape-set flexure may be used in combination with an outer shaft, such that extension of the flexure from the shaft allows the shape-set flexure to reach farther to one side as well as articulate in the opposite direction.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A medical device comprising:
 a. an elongated body for use in medical procedures, the elongated body having a neutral axis and comprising:
  i. a spine along the length of the elongated body;
  ii. a series of ribs along the length of the elongated body, wherein the series of ribs form a corresponding series of ribbed voids along the length of the elongated body, wherein the elongated body, the spine, and the ribs are formed as a single component; and
  iii. a lumen longitudinally oriented within the elongated body, wherein the lumen has a non-cylindrical cross-section defined by walls of uneven thickness formed from the elongated body and having a narrowed mid-section;
 b. an ancillary component positioned within the lumen along the length of the body; and c. a control wire that is configured to actuate an end effector that is operatively coupled to the control wire, wherein the control wire is positioned within the lumen offset from the neutral axis of the elongated body and separated from the ancillary component within the lumen by the narrowed mid-section.

2. The device of claim 1, wherein the spine is solid along the length of the elongated body.

3. The device of claim 1, wherein the series of ribs and the series of ribbed voids are formed along the length of the elongated body opposite the spine, and wherein the spine comprises a series of spinal ribs that form a series of corresponding spinal voids.

4. The device of claim 3, wherein the ribs contain eyelets configured to convey an ancillary component along the length of the elongated body.

5. The device of claim 1, wherein the ribbed voids are teardrop-shaped.

6. The device of claim 1, wherein the series of ribbed voids are formed along a single lateral edge of the elongated body and centered along a line along the length of the elongated body opposite the spine.

7. The device of claim 1, wherein the ancillary component comprises a forceps tool that is positioned within the lumen.

8. The device of claim 1, wherein the control wire is positioned within the lumen offset from the neutral axis of the elongated body and oriented away from the spine along the length of the elongated body.

9. The device of claim 1, wherein the control wire comprises a pull wire that is configured to articulate the elongated body.

10. The device of claim 1, wherein the ancillary component is positioned within the lumen and oriented toward the spine along the length of the elongated body.

11. The device of claim 1, wherein the lumen comprises an upper region and a lower region.

12. The device of claim 11, wherein the ancillary component is positioned within the upper region of the lumen and the control wire is positioned within the lower region.

13. The device of claim 1, wherein the lumen is configured to convey a plurality of ancillary components.

14. The device of claim 1, further comprising:
a. a shaft, comprising a distal end and proximal end;
b. wherein the elongated body is aligned longitudinally within the shaft, and the elongated body is configured to extend from the distal end of the shaft.

15. A method for performing medical procedures comprising:
a. directing an elongated tool towards an operative site, the tool comprising a proximal portion and distal portion;
b. extending a longitudinally-aligned elongated body from the distal portion of the tool; and
c. articulating the elongated body towards the operative site;
d. wherein the elongated body has a neutral axis and comprises:
  i. a spine along the length of the elongated body;
  ii. a series of ribs along the length of the elongated body, wherein the series of ribs form a corresponding series of voids along the length of the elongated body, and wherein the elongated body, the spine, and the ribs are formed as a single component; and
  iii. a lumen longitudinally oriented within the elongated body,
wherein the lumen has a non-cylindrical cross-section defined by walls of uneven thickness formed from the elongated body and having a narrowed mid-section,
wherein an ancillary component is positioned within the lumen along the length of the body, and
wherein a control wire configured to actuate an end effector that is operatively coupled to the control wire is positioned within the lumen, the control wire being offset from the neutral axis of the elongated body and separated from the ancillary component within the lumen by the narrowed mid-section.

16. The method of claim 15, wherein the tool is a flexible shaft.

17. The method of claim 15, wherein the series of ribs and the series of ribbed voids are formed along the length of the elongated body opposite the spine, and wherein the spine comprises a series of spinal ribs that form a series of corresponding spinal voids.

18. The method of claim 15, wherein the lumen is configured to convey an ancillary component along the length of the elongated body.

* * * * *